United States Patent
Wagner et al.

(10) Patent No.: US 9,623,241 B2
(45) Date of Patent: Apr. 18, 2017

(54) TREATMENT METHODS

(75) Inventors: Timothy Andrew Wagner, Cambridge, MA (US); Felipe Fregni, Chestnut Hill, MA (US)

(73) Assignee: Highland Instruments, Somerville, MA (US)

( * ) Notice: Subject to any disclaimer, the term of this patent is extended or adjusted under 35 U.S.C. 154(b) by 692 days.

(21) Appl. No.: 13/102,476

(22) Filed: May 6, 2011

(65) Prior Publication Data

US 2011/0245734 A1 Oct. 6, 2011

Related U.S. Application Data

(63) Continuation-in-part of application No. 11/764,468, filed on Jun. 18, 2007, now Pat. No. 8,929,979.

(60) Provisional application No. 60/814,843, filed on Jun. 19, 2006, provisional application No. 61/378,328, filed on Aug. 30, 2010.

(51) Int. Cl.
| | |
|---|---|
| *A61N 1/36* | (2006.01) |
| *A61N 7/00* | (2006.01) |
| *A61N 5/06* | (2006.01) |
| *A61F 7/00* | (2006.01) |
| *A61N 2/00* | (2006.01) |

(52) U.S. Cl.
CPC ..... *A61N 1/36025* (2013.01); *A61N 1/36021* (2013.01); *A61N 7/00* (2013.01); *A61N 2/004* (2013.01); *A61N 2007/0026* (2013.01)

(58) Field of Classification Search
CPC ........... A61N 1/36014; A61N 1/36071; A61N 2007/0026; A61N 7/00; A61N 1/36017; A61N 1/36025; A61N 1/36064; A61N 1/36089; A61N 1/361; A61N 1/36103; A61N 2/004; A61N 1/36082; A61N 1/36021
USPC ....................... 607/2–3, 46; 601/2
See application file for complete search history.

(56) References Cited

U.S. PATENT DOCUMENTS

| | | | |
|---|---|---|---|
| 4,709,700 | A | 12/1987 | Hyrman |
| 4,989,605 | A | 2/1991 | Rossen |
| 5,476,438 | A | 12/1995 | Edrich et al. |
| 5,551,953 | A | 9/1996 | Lattin et al. |
| 5,738,625 | A | 4/1998 | Gluck |
| 5,895,416 | A | 4/1999 | Barreras, Sr. et al. |
| 6,021,348 | A | 2/2000 | James |
| 6,066,084 | A | 5/2000 | Edrich et al. |

(Continued)

FOREIGN PATENT DOCUMENTS

| | | |
|---|---|---|
| WO | 2006/027757 A2 | 3/2006 |
| WO | 2007/149811 A2 | 12/2007 |

(Continued)

OTHER PUBLICATIONS

Extended European Search Report for Application No. 12826175.7 dated Mar. 9, 2015 (6 pages).

(Continued)

*Primary Examiner* — Mark W Bockelman
(74) *Attorney, Agent, or Firm* — Adam M. Schoen; Brown Rudnick LLP

(57) ABSTRACT

The invention generally relates to methods for treating osteoarthritis. In certain embodiments, methods of the invention involve providing stimulation to a subject's central nervous system to modulate a signal sent to or from the subject's joint, thereby treating osteoarthritis.

8 Claims, 6 Drawing Sheets

FIG. 1a

(56) References Cited

U.S. PATENT DOCUMENTS

| | | | |
|---|---|---|---|
| 6,221,908 B1 | 4/2001 | Kilgard et al. | |
| 6,231,527 B1 | 5/2001 | Sol | |
| 6,234,953 B1 | 5/2001 | Thomas et al. | |
| 6,520,903 B1 | 2/2003 | Yamashiro | |
| 6,520,911 B1 | 2/2003 | Wen | |
| 6,645,144 B1 | 11/2003 | Wen et al. | |
| 6,764,498 B2 | 7/2004 | Mische | |
| 6,887,239 B2 | 5/2005 | Elstrom et al. | |
| 7,146,210 B2 | 12/2006 | Palti | |
| 7,937,152 B1* | 5/2011 | Lozano | 607/46 |
| 8,718,758 B2 | 5/2014 | Wagner et al. | |
| 8,929,979 B2 | 1/2015 | Wagner et al. | |
| 2001/0051774 A1 | 12/2001 | Littrup et al. | |
| 2004/0131998 A1 | 7/2004 | Marom et al. | |
| 2005/0003380 A1 | 1/2005 | Cohen et al. | |
| 2005/0043726 A1 | 2/2005 | McHale et al. | |
| 2005/0043762 A1 | 2/2005 | Echt et al. | |
| 2005/0202489 A1 | 9/2005 | Cho et al. | |
| 2006/0004422 A1 | 1/2006 | De Ridder | |
| 2006/0017749 A1 | 1/2006 | McIntyre et al. | |
| 2006/0247104 A1 | 11/2006 | Grabiner et al. | |
| 2006/0257893 A1 | 11/2006 | Takahashi et al. | |
| 2007/0060974 A1 | 3/2007 | Lozano | |
| 2007/0156180 A1 | 7/2007 | Jaax et al. | |
| 2008/0046053 A1* | 2/2008 | Wagner et al. | 607/116 |
| 2008/0124726 A1 | 5/2008 | Monforte | |
| 2008/0228110 A1 | 9/2008 | Berme | |
| 2009/0157141 A1* | 6/2009 | Chiao et al. | 607/46 |
| 2009/0240170 A1 | 9/2009 | Rowley et al. | |
| 2010/0268287 A1 | 10/2010 | Celnik | |
| 2011/0275927 A1 | 11/2011 | Wagner et al. | |

FOREIGN PATENT DOCUMENTS

| | | |
|---|---|---|
| WO | 2010/009141 A1 | 1/2010 |
| WO | 2010/017392 A2 | 2/2010 |
| WO | 2012/101093 A2 | 8/2012 |
| WO | 2013/054257 A1 | 4/2013 |

OTHER PUBLICATIONS

Extended Supplementary European Search Report for Application No./Patent No. 12752660.6 dated Jul. 9, 2014 (6 pages).

* cited by examiner

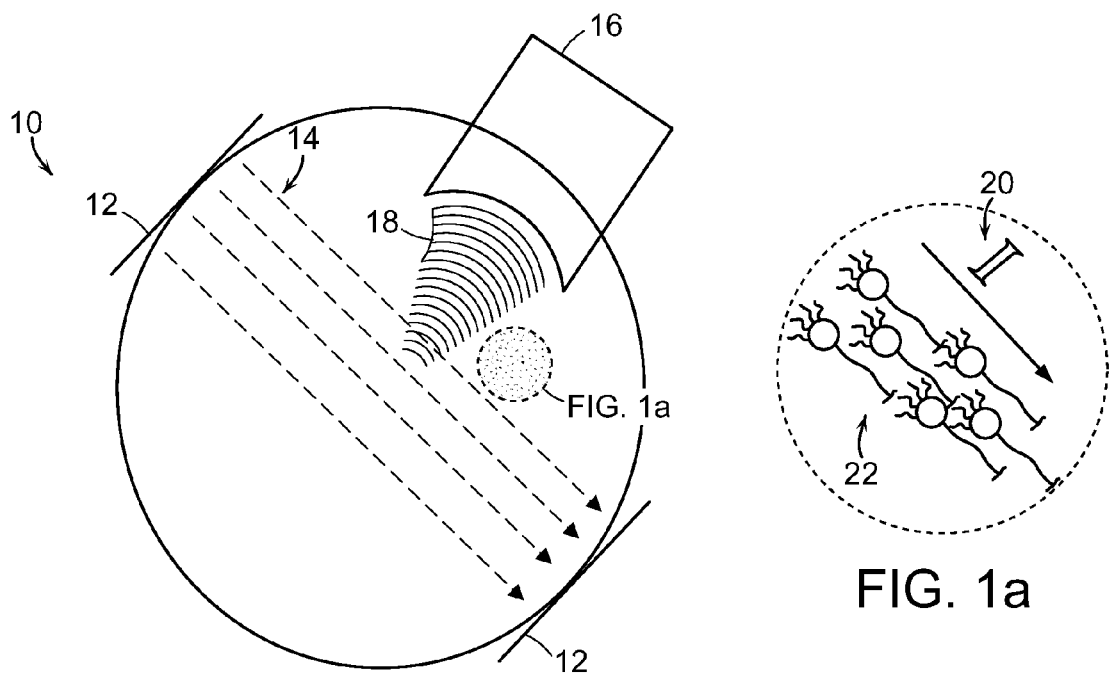
FIG. 1
FIG. 1a
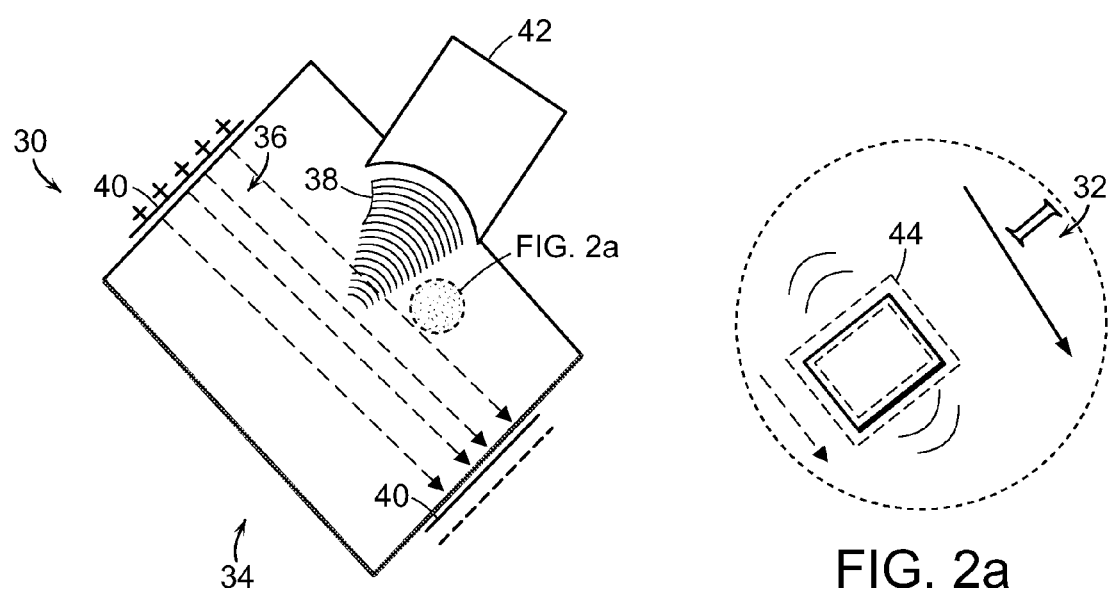
FIG. 2
FIG. 2a

TREATMENT METHODS

RELATED APPLICATIONS

The present application is a continuation-in-part of U.S. nonprovisional application Ser. No. 11/764,468, filed Jun. 18, 2007, which claims the benefit of and priority to U.S. provisional application Ser. No. 60/814,843, filed Jun. 19, 2006. The present application also claims the benefit of and priority to U.S. provisional application Ser. No. 61/378,328, filed Aug. 30, 2010. The content of each application is incorporated by reference herein in its entirety.

FIELD OF THE INVENTION

The invention generally relates to methods for treating osteoarthritis.

BACKGROUND

Osteoarthritis is a progressive disorder of the joints caused by loss of cartilage and is the most common form of arthritis. The loss of cartilage may result from a person's joint wearing down over time or through a sudden injury to the joint (e.g. through normal use, sudden injury/trauma, repetitive stress injuries, septic arthritis, repeated episodes of gout, poor posture, metabolic disorders, or secondary to obesity).

The loss of cartilage allows bones to rub together, causing pain, swelling, and loss of motion of the joint. As the cartilage is worn away, the bone forms spurs, areas of abnormal hardening, and fluid-filled pockets in the marrow known as subchondral cysts. As the disorder progresses, pain and inflammation results from deformation of the bones and fluid accumulation in the joints. As the injury worsens, the nervous system tunes to the pain signal. For instance osteoarthritis pain might be caused by degeneration of a person's knee, but the pain signal travels from the knee to the person's spinal cord and ultimately to the person's brain. During the course of osteoarthritis, the spinal cord and brain both become more sensitive to the pain signals, essentially becoming more efficient at processing the signals sent from the knee and amplifying the perception of the pain. Specifically, a chronic pain signal from an injured joint leads to peripheral pain receptors becoming sensitized to an injury. The chronic pain signal causes changes at the spinal cord that amplify electrical activity and the pain signal that is sent to the brain. The amplified pain signal sent to the brain results in increased activity in select regions of the brain, leading to central sensitization, i.e., increased pain perception, and amplified facilitory output from the brain. Osteoarthritis gradually worsens with time, however, treatment can relieve pain and allow a person to live a normal and active lifestyle.

SUMMARY

The invention generally relates to methods for treating osteoarthritis. Methods of the invention focus stimulation in select regions of the central nervous system (e.g., brain and/or spinal cord) to block processing of pain signals received by the brain from an injured joint or perpetuated in the brain once received. In this manner, methods of the invention prevent central sensitization of the pain signal in a person's brain and provide effective therapeutic relief from the pain signal sent from osteoarthritis damaged joints. Further, elimination of the pain signal breaks the cyclic feedback loop between the injured joint and the brain and leads to reduction in inflammation of the injured joint, thereby treating osteoarthritis.

Certain aspects of the invention generally relate to methods for treating osteoarthritis that involve providing stimulation to a subject's central nervous system (e.g., brain or spinal cord) to modulate a signal sent to or from the subject's joint, thereby treating osteoarthritis. Exemplary signals that are modulated include pain related signals or inflammatory related signals. However, methods of the invention may modulate any type of signal sent from a subject's joint and are not limited to those exemplary signals. Generally, the signal will be processed in the subject's brain. However, the signal may be processed in other parts of the subject's body, e.g., the spinal cord. In certain embodiments, affects of the stimulation alter neural function past the duration of stimulation. Thus, the affects of the treatment last significantly longer than the period of treatment.

Any type of stimulation known in the art may be used with methods of the invention, and the stimulation may be provided in any clinically acceptable manner. For example, the stimulation may be provided invasively or noninvasively. Preferably, the stimulation is provided in a noninvasive manner. For example, electrodes may be configured to be applied to the specified tissue, tissues, or adjacent tissues. As one alternative, the electric source may be implanted inside the specified tissue, tissues, or adjacent tissues.

Exemplary types of stimulation include mechanical, optical, electromagnetic, thermal, or a combination thereof. In particular embodiments, the stimulation is a mechanical field (i.e., acoustic field), such as that produced by an ultrasound device. In other embodiments, the stimulation is an electrical field. In other embodiments, the stimulation is an magnetic field. Other exemplary types of stimulation include Transcranial Direct Current Stimulation (TDCS), Transcranial Ultrasound (TUS)/Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). Other exemplary types include implant methods such as deep brain stimulation (DBS), microstimulation, spinal cord stimulation (SCS), and vagal nerve stimulation (VNS). In other embodiments, the stimulation source may work in part through the alteration of the nervous tissue electromagnetic properties, where stimulation occurs from an electric source capable of generating an electric field across a region of tissue and a means for altering the permittivity of tissue relative to the electric field, whereby the alteration of the tissue permittivity relative to the electric field generates a displacement current in the tissue. The means for altering the permittivity may include a chemical source, optical source, mechanical source, thermal source, or electromagnetic source.

In other embodiments, the stimulation is provided by a combination of an electric field and a mechanical field. The electric field may be pulsed, time varying, pulsed a plurality of time with each pulse being for a different length of time, or time invariant. Generally, the electric source is current that has a frequency from about DC to approximately 100,000 Hz. The mechanical field may be pulsed, time varying, or pulsed a plurality of time with each pulse being for a different length of time. In certain embodiments, the electric field is a DC electric field.

The stimulation may be applied to a structure or multiple structures within the brain or the nervous system. Exemplary structures include dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and spinal cord.

In one exemplary embodiment, the electric field is applied broadly and mechanical field is focused on a specific brain structure or multiple structures for therapeutic purposes. The electric field may be applied broadly and the mechanical field may be focused on a structure or multiple structures, such as brain or nervous tissues including dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and/or spinal cord. Other possible configurations include applying both the electrical field and the mechanical field in a broad manner; applying both the electric field and the mechanical field in a focused manner; or applying the electric field in a focused manner and the mechanical field in a broad manner.

Other aspects of the invention provide methods for treating osteoarthritis that involve providing stimulation to a subject's brain or central nervous system to modulate a pain related signal to or from the subject's periphery, thereby treating osteoarthritis.

Another aspect of the invention provides methods for treating osteoarthritis that involve generating an electric field across a region of neural tissue, and generating a mechanical field across the region of neural tissue, whereby the combined effects of the electric field and the mechanical field generate a current in the neural tissue that modulates a signal sent to a joint.

Another aspect of the invention provides methods for treating osteoarthritis that involve providing a noninvasive transcranial neural stimulator that includes a noninvasive transcranial electric stimulator capable of generating an electric field across a region of neural tissue, and a noninvasive transcranial ultrasound device capable of generating a mechanical field across the region of neural tissue, whereby the combined effects of the electric field and the mechanical field generate a current in the neural tissue; and applying the stimulator to the neural tissue to modulate a signal sent to a joint, thereby treating osteoarthritis.

Another aspect of the invention provides methods for treating osteoarthritis that involve providing a noninvasive transcranial neural stimulator, and using the stimulator to treating osteoarthritis.

Another aspect of this invention is related to integrating stimulation with mechanisms that are used to monitor a patient's response to the stimulation and/or to fine tune the stimulation parameters (e.g. imaging, biofeedback, physiological response) for maximum clinical effect.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein:

FIG. 1 is a plan view of one embodiment of an apparatus for stimulating biological tissue constructed in accordance with the principles of the present disclosure;

FIG. 2 is a top plan view of an exemplary embodiment of an apparatus for stimulating biological tissue constructed in accordance with the principles of the present disclosure;

DETAILED DESCRIPTION

Figure 3:
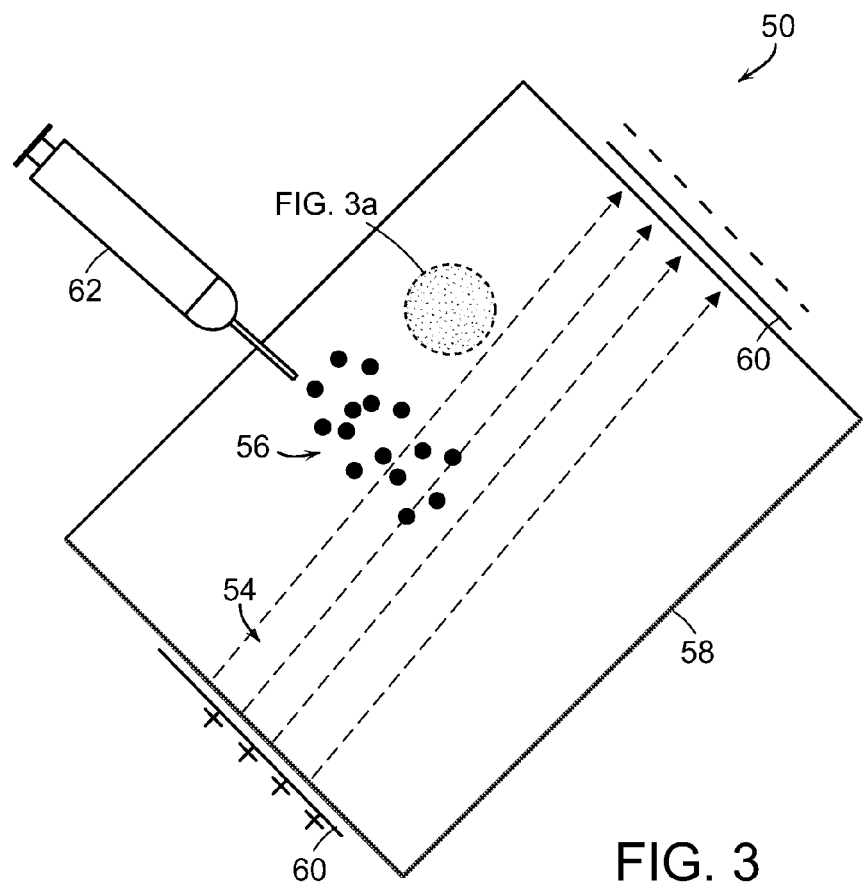
FIG. 3 is a top plan view of an exemplary embodiment of an apparatus for stimulating biological tissue implementing a chemical source for altering permittivity constructed in accordance with the principles of the present disclosure.
Figure 3A:
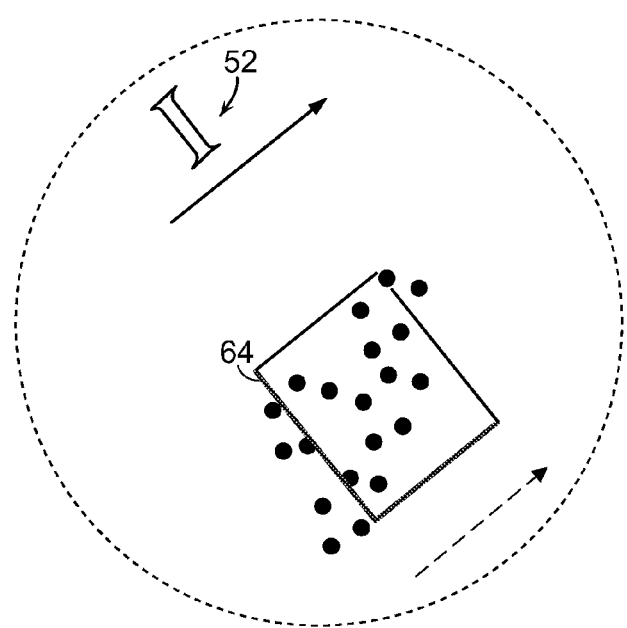

It is envisioned that the present disclosure may be used to stimulate biological tissue in-vivo comprising an electric source that is placed on the body to generate an electric field and a means for altering the permittivity of tissue relative to the electric field, whereby the alteration of the tissue permittivity relative to the electric field generates a displacement current in the tissue. The exemplary embodiments of the apparatuses and methods disclosed can be employed in the area of neural stimulation, where amplified, focused, direction altered, and/or attenuated currents could be used to alter neural activity via directly stimulating neurons, depolarizing neurons, hyperpolarizing neurons, modifying neural membrane potentials, altering the level of neural cell excitability, and/or altering the likelihood of a neural cell firing. Likewise, the method for stimulating biological tissue may also be employed in the area of muscular stimulation, including cardiac stimulation, where amplified, focused, direction altered, and/or attenuated currents could be used to alter muscular activity via direct stimulation, depolarizing muscle cells, hyperpolarizing muscle cells, modifying membrane potentials, altering the level of muscle cell excitability, and/or altering the likelihood of cell firing. Similarly, it is envisioned that the present disclosure may be employed in the area of cellular metabolism, physical therapy, drug delivery, and gene therapy.

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

The components of the tissue stimulation method according to the present disclosure are fabricated from materials suitable for a variety medical applications, such as, for example, polymerics, gels, films, and/or metals, depending on the particular application and/or preference. Semi-rigid and rigid polymerics are contemplated for fabrication, as well as resilient materials, such as molded medical grade polyurethane, as well as flexible or malleable materials. The motors, gearing, electronics, power components, electrodes, and transducers of the method may be fabricated from those suitable for a variety of medical applications. The method according to the present disclosure may also include circuit boards, circuitry, processor components, etc. for computerized control. One skilled in the art, however, will realize that other materials and fabrication methods suitable for assembly and manufacture, in accordance with the present disclosure, also would be appropriate.

The following discussion includes a description of the components and exemplary methods for generating currents in biological tissues in accordance with the principles of the present disclosure. Alternate embodiments are also disclosed. Reference will now be made in detail to the exemplary embodiments of the present disclosure illustrated in the accompanying figures wherein like reference numerals indicate the similar parts throughout the figures.

Turning now to FIG. 1, which illustrates an exemplary embodiment of an apparatus 10 to alter currents, e.g., amplify, focus, alter direction, and/or attenuate in the presence of an applied electric field or applied current source by the combined application of a mechanical field within a biological material to stimulate the biological cells and/or tissue in accordance with the present disclosure. For example, the apparatus 10 illustrated in FIG. 1 according to the present disclosure may be applied to the area of neural stimulation. An initial source electric field 14 results in a current in the tissue. The electric field 14 is created by an electric source, current or voltage source. As described in further detail below, the permittivity of the tissue is altered relative to the electric field, for example by a mechanical field, thereby generating an additional displacement current.

Electrodes 12 are applied to the scalp and generate a low magnitude electric field 14 over a large brain region. While electrodes 12 are used and applied to the scalp in this exemplary embodiment, it is envisioned that the electrodes may be applied to a number of different areas on the body including areas around the scalp. It is also envisioned that one electrode may be placed proximal to the tissue being stimulated and the other distant, such as one electrode on the scalp and one on the thorax. It is further envisioned that electric source could be mono-polar with just a single electrode, or multi-polar with multiple electrodes. Similarly, the electric source may be applied to tissue via any medically acceptable medium. It is also envisioned that means could be used where the electric source does not need to be in direct contact with the tissue, such as for example, inductive magnetic sources where the entire tissue region is placed within a large solenoid generating magnetic fields or near a coil generating magnetic fields, where the magnetic fields induce electric currents in the tissue.

The electric source may be direct current (DC) or alternating current (AC) and may be applied inside or outside the tissue of interest. Additionally, the source may be time varying. Similarly, the source may be pulsed and may be comprised of time varying pulse forms. The source may be an impulse. Also, the source according to the present disclosure may be intermittent.

A mechanical source such as an ultrasound source 16 is applied on the scalp and provides concentrated acoustic energy 18, i.e., mechanical field to a focused region of neural tissue, affecting a smaller number of neurons 22 than affected by the electric field 14, by the mechanical field 18 altering the tissue permittivity relative to the applied electric field 14, and thereby generating the altered current 20. The mechanical source may be any acoustic source such as an ultrasound device. Generally, such device may be a device composed of electromechanical transducers capable of converting an electrical signal to mechanical energy such as those containing piezoelectric materials, a device composed of electromechanical transducers capable of converting an electrical signal to mechanical energy such as those in an acoustic speaker that implement electromagnets, a device in which the mechanical source is coupled to a separate mechanical apparatus that drives the system, or any similar device capable of converting chemical, plasma, electrical, nuclear, or thermal energy to mechanical energy and generating a mechanical field.

Furthermore, the mechanical field could be generated via an ultrasound transducer that could be used for imaging tissue. The mechanical field may be coupled to tissue via a bridging medium, such as a container of saline to assist in the focusing or through gels and/or pastes which alter the acoustic impedance between the mechanical source and the tissue. The mechanical field may be time varying, pulsed, an impulse, or may be comprised of time varying pulse forms. It is envisioned that the mechanical source may be applied inside or outside of the tissue of interest. There are no limitations as to the frequencies that can be applied via the mechanical source, however, exemplary mechanical field frequencies range from the sub kHZ to 1000s of MHz. Additionally, multiple transducers providing multiple mechanical fields with similar or differing frequencies, and/or similar or different mechanical field waveforms may be used-such as in an array of sources like those used in focused ultrasound arrays. Similarly, multiple varied electric fields could also be applied. The combined fields, electric and mechanical, may be controlled intermittently to cause specific patterns of spiking activity or alterations in neural excitability. For example, the device may produce a periodic signal at a fixed frequency, or high frequency signals at a pulsed frequency to cause stimulation at pulse frequencies shown to be effective in treating numerous pathologies. Such stimulation waveforms may be those implemented in rapid or theta burst TMS treatments, deep brain stimulation treatments, epidural brain stimulation treatments, spinal cord stimulation treatments, or for peripheral electrical stimulation nerve treatments. The ultrasound source may be placed at any location relative to the electrode locations, i.e., within, on top of, below, or outside the same location as the electrodes as long as components of the electric field and mechanical field are in the same region. The locations of the sources should be relative to each other such that the fields intersect relative to the tissue and cells to be stimulated, or to direct the current alteration relative to the cellular components being stimulated.

The apparatus and method according to the present disclosure generates capacitive currents via permittivity alterations, which can be significant in magnitude, especially in the presence of low frequency applied electric fields. Tissue permittivities in biological tissues are much higher than most other non biological materials, especially for low frequency applied electric fields where the penetration depths of electric fields are highest. This is because the permittivity is inversely related to the frequency of the applied electric field, such that the tissue permittivity magnitude is higher with lower frequencies. For example, for electric field frequencies below 100,000 Hz, brain tissue has permittivity magnitudes as high as or greater than $10^8$ (100,000,000) times the permittivity of free space ($8.854*10^{-12}$ farad per meter), and as such, minimal local perturbations of the relative magnitude can lead to significant displacement current generation. As the frequency of the electric field increases, the relative permittivity decreases by orders of magnitude, dropping to magnitudes of approximately $10^3$ times the permittivity of free space ($8.854*10^{-12}$ farad per meter) for electric field frequencies of approximately 100,000 Hz. Additionally, by not being constrained to higher electric field frequencies, the method according to the present disclosure is an advantageous method for stimulating biological tissue due to lowered penetration depth limitations and thus lowered field strength requirements. Additionally, because displacement currents are generated in the area of the permittivity change, focusing can be accomplished via the ultrasound alone. For example, to generate capacitive currents via a permittivity perturbation relative to an applied electric field as described above, broad DC or a low frequency electric source field well below the cellular stimulation threshold is applied to a brain region but stimulation effects are locally focused in a smaller region by altering the tissue permittivity in the focused region of a mechanical field generated by a mechanical source such as an ultrasound source. This could be done noninvasively with the electrodes and the ultrasound device both placed on the scalp surface such that the fields penetrate the tissue surrounding the brain region and intersect in the targeted brain location, or with one or both of the electrodes and/or the ultrasound device implanted below the scalp surface (in the brain or any of the surrounding tissue) such that the fields intersect in the targeted region.

A displacement current is generated by the modification of the permittivity in the presence of the sub threshold electric field and provides a stimulatory signal. In addition to the main permittivity change that occurs in the tissues, which is responsible for stimulation (i.e., the generation of the altered currents for stimulation), a conductivity change could also occur in the tissue, which secondarily alters the ohmic component of the currents. In a further embodiment, the displacement current generation and altered ohmic current components may combine for stimulation. Generally, tissue conductivities vary slightly as a function of the applied electric field frequency over the DC to 100,000 Hz frequency range, but not to the same degree as the permittivities, and increase with the increasing frequency of the applied electric field. Additionally in biological tissues, unlike other materials, the conductivity and permittivity do not show a simple one-to-one relationship as a function of the applied electric field frequency. The permittivity ranges are as discussed above.

Although the process described may be accomplished at any frequency of the applied electric field, the method in an exemplary embodiment is applied with lower frequency applied electric fields due to the fact the permittivity magnitudes of tissues, as high as or greater than $10^8$ times the permittivity of free space, and the electric field penetration depths are highest for low frequency applied electric fields. Higher frequency applied electric fields may be less desirable as they will require greater radiation power to penetrate the tissue and/or a more pronounced mechanical source for permittivity alteration to achieve the same relative tissue permittivity change, i.e., at higher applied electric field frequencies the permittivity of the tissue is lower and as such would need a greater overall perturbation to have the same overall change in permittivity of a tissue as at a lower frequency. Applied electric field frequencies in the range of DC to approximately 100,000 Hz frequencies are advantageous due to the high tissue permittivity in this frequency band and the high penetration depth for biological tissues at these frequencies. In this band, tissues are within the so called 'alpha dispersion band' where relative tissue permittivity magnitudes are maximally elevated (i.e., as high as or greater than $10^8$ times the permittivity of free space). Frequencies above approximately 100,000 to 1,000,000 Hz for the applied electric fields are still applicable for the method described in generating displacement currents for the stimulation of biologic cells and tissue, however, both the tissue permittivity and penetration depth are limited for biological tissues in this band compared to the previous band but displacement currents of sufficient magnitude can still be generated for some applications. In this range, the magnitude of the applied electric field will likely need to be increased, or the method used to alter the permittivity relative to the applied electric field increased to bring about a greater permittivity change, relative to the tissue's permittivity magnitude for the applied electric field frequency. Additionally, due to potential safety concerns for some applications, it may be necessary to limit the time of application of the fields or to pulse the fields, as opposed to the continuous application that is possible in the prior band. For tissues or applications where the safety concerns preclude the technique in deeper tissues, the technique could still be applied in more superficial applications in a noninvasive manner or via an invasive method. Higher frequency applied electric fields, above 1,000,000 to 100,000,000 Hz, could be used in generating displacement currents for the stimulation of biologic cells and tissue. However, this would require a more sufficient permittivity alteration or electromagnetic radiation, and as such is less than ideal in terms of safety than the earlier bands. For frequencies of the applied electric field above 100,000,000 Hz, biologic cell and tissue stimulation may still be possible, but may be limited for specialized applications that require less significant displacement currents.

The focus of the electric and mechanical fields to generate an altered current according to the present disclosure may be directed to various structures within the brain or nervous system including but not limited to dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, spinal cord, nerve roots, sensory organs, and peripheral nerves.

The focused tissue may be selected such that a wide variety of pathologies may be treated. Such pathologies that may be treated include but are not limited to Multiple Sclerosis, Amyotrophic Lateral Sclerosis, Alzheimer's Disease, Dystonia, Tics, Spinal Cord Injury, Traumatic Brain Injury, Drug Craving, Food Craving, Alcohol Craving, Nicotine Craving, Stuttering, Tinnitus, Spasticity, Parkinson's Disease, Parkinsonianism, Obsessions, Depression, Schizophrenia, Bipolar Disorder, Acute Mania, Catonia, Post-Traumatic Stress Disorder, Autism, Chronic Pain Syndrome, Phantom Limb Pain, Epilepsy, Stroke, Auditory Hallucinations, Movement Disorders, Neurodegenerative Disorders, Pain Disorders, Metabolic Disorders, Addictive Disorders, Psychiatric Disorders, Traumatic Nerve Injury, and Sensory Disorders. Furthermore, electric and mechanical fields to generate an altered current may be focused on specific brain or neural structures to enact procedures including sensory augmentation, sensory alteration, anesthesia induction and maintenance, brain mapping, epileptic mapping, neural atrophy reduction, neuroprosthetic interaction or control with nervous system, stroke and traumatic injury neurorehabilitation, bladder control, assisting breathing, cardiac pacing, muscle stimulation, and treatment of pain syndromes, such as those caused by migraine, neuropathies, and low-back pain; or internal visceral diseases, such as chronic pancreatitis or cancer. The methods herein could be expanded to any form of arthritis, impingement disorders, overuse injuries, entrapment disorders, and/or any muscle, skeletal, or connective tissue disorder which leads to chronic pain, central sensitization of the pain signals, and/or an inflammatory response.

In the focused region of tissue to which the mechanical fields are delivered, the excitability of individual neurons can be heightened to the point that the neurons can be stimulated by the combined fields, or be affected such as to cause or amplify the alteration of the neural excitability caused by the altered currents, either through an increase or decrease in the excitability of the neurons. This alteration of neural excitability can last past the duration of stimulation and thus be used as a basis to provide lasting treatment. Additionally, the combined fields can be provided in multiple, but separate sessions to have a summed, or carry-over effect, on the excitability of the cells and tissue. The combined fields can be provided prior to another form of stimulation, to prime the tissue making it more or less susceptible to alternate, follow-up forms of stimulation. Furthermore, the combined fields can be provided after an alternate form of stimulation, where the alternate form of stimulation is used to prime the tissue to make it more or less susceptible to the form of stimulation disclosed herein. Furthermore, the combined fields could be applied for a chronic period of time.

FIG. 2 illustrates a set up 30 to perform a method for generating an altered current with a newly generated displacement current 32 for stimulation in biologic tissue 34 through the combined effects of an electric field 36 and a mechanical field 38. A tissue or composite of tissues 34 is placed adjacent to the anode and cathode of an electric source 40 which generates an electric field 36. The electric field 36 is combined with a mechanical, e.g., ultrasound field 38 which can be focused on the tissue 34 and generated via an ultrasound transducer 42. In a sub-region of tissue 44 where the mechanical field 38 is focused and intersects with the electric field 36, a displacement current 32 is generated. By vibrating and/or mechanically perturbing the sub-region of tissue 44, the permittivity of the tissue 44 can be altered relative to the applied electric field 36 to generate a displacement current 32 in addition to the current that would be present due to the source electric field 36 and altered due to conductivity changes in the tissue caused by the mechanical perturbation.

By providing the mechanical field 38 to the sub region of tissue 44, the permittivity can be altered within the electric field 36 by either new elements of the sub region of tissue 44 vibrating in and out of the electric field such that the continuum permittivity of the tissue is changed relative to the electric field 36, or that the bulk properties of the sub region of tissue 44 and the permittivity, or tissue capacitance, change due to the mechanical perturbation. An example of altering the permittivity within the electric field can occur when a cell membrane and extra-cellular fluid, both of different permittivities, are altered in position relative to the electric field by the mechanical field. This movement of tissues of different permittivity relative to the electric field will generate a new displacement current. The tissues could have permittivity values as high as or greater than 10^8 times the permittivity of free space, differ by orders of magnitude, and/or have anisotropic properties such that the tissue itself demonstrates a different permittivity magnitude depending on the relative direction of the applied electric field. An example of altering permittivity of the bulk tissue occurs where the relative permittivity constant of the bulk tissue is directly altered by mechanical perturbation in the presence of an electric field. The mechanical source, i.e., ultrasound source may be placed at any location relative to the electrode locations, i.e., within or outside the same location as the electrodes, as long as components of the electric field and mechanical field are in the same region.

Tissue permittivities can be altered relative to the applied electric fields via a number of methods. Mechanical techniques can be used to either alter the bulk tissue permittivity relative to an applied electric field or move tissue components of differing permittivities relative to an applied electric field. There are no specific limitations to the frequency of the mechanical field that is applied as previously discussed, however, exemplary frequencies range from the sub kHZ to 1000s of MHz. A second electromagnetic field could be applied to the tissue, at a different frequency than the initial frequency of the applied electromagnetic field, such that it alters the tissue permittivity at the frequency dependent point of the initially applied electric field. An optical signal could also be focused on the tissues to alter the permittivity of the tissue relative to an applied electric field. A chemical agent or thermal field could also be applied to the tissues to alter the permittivity of the tissue relative to an applied electric field. These methods could also be used in combination to alter the tissue permittivity relative to an applied electric field via invasive or noninvasive methods.

For example, FIG. 3 shows a set up 50 for generating an altered current with a newly generated displacement current 52 through the combined effects of an electric field 54 and a chemical agent 56. A tissue or composite of tissues 58 is placed within an electric source 60 which generates an electric field 54 and combined with chemical source 62 which releases a chemical agent 56 that can be focused on the tissue 58. In the area that the chemical agent 56 is released in the tissue 64, the electric field 54 transects the sub region of tissue 64, and the chemical agent 56 reacts with the sub region of tissue 64 to alter the tissue's relative permittivity relative to the applied electric field 54. This generates a displacement current 52 in addition to the current that would be present due to the source electric field 54. The chemical agent 56 may be any agent which can react with the tissue or cellular components of the tissue 64 to alter its permittivity relative to the electric field 54. This may be by a thermoreactive process to raise or lower the tissue 64 temperature or through a chemical reaction which alters the distribution of ions in the cellular and extra-cellular media, for instance, along ionic double layers at cell walls in the tissue 64. Similarly, the conformation of proteins and other charged components within the tissue 64 could be altered such that the permittivity of the tissue is altered relative to the low frequency electric field 54. The agent could also be any agent that adapts the permanent dipole moments of any molecules or compounds in the tissue 64, temporarily or permanently relative to the low frequency electric field 54. The chemical reaction driven by the chemical agent 56 must work rapidly enough such that the permittivity of the tissue is quickly altered in the presence of the electric field 54 in order to generate the displacement current 52. The reaction may also be such as to fluctuate the permittivity, such that as the permittivity continues to change displacement currents continue to be generated. In addition to the main permittivity change that occurs in the tissues, a conductivity change could also occur in the tissue, which secondarily alters the ohmic component of the currents. A biological agent may be used in place of, or in addition to, the chemical agent 56. This embodiment may have particular application for focused drug delivery where an additional chemical or biological agent is included to assist in therapy of the tissue, or where the altered current could drive an additional electrochemical reaction for therapy. For example, this could be used in areas such as focused gene therapy or focused chemotherapy.

Figure 4:
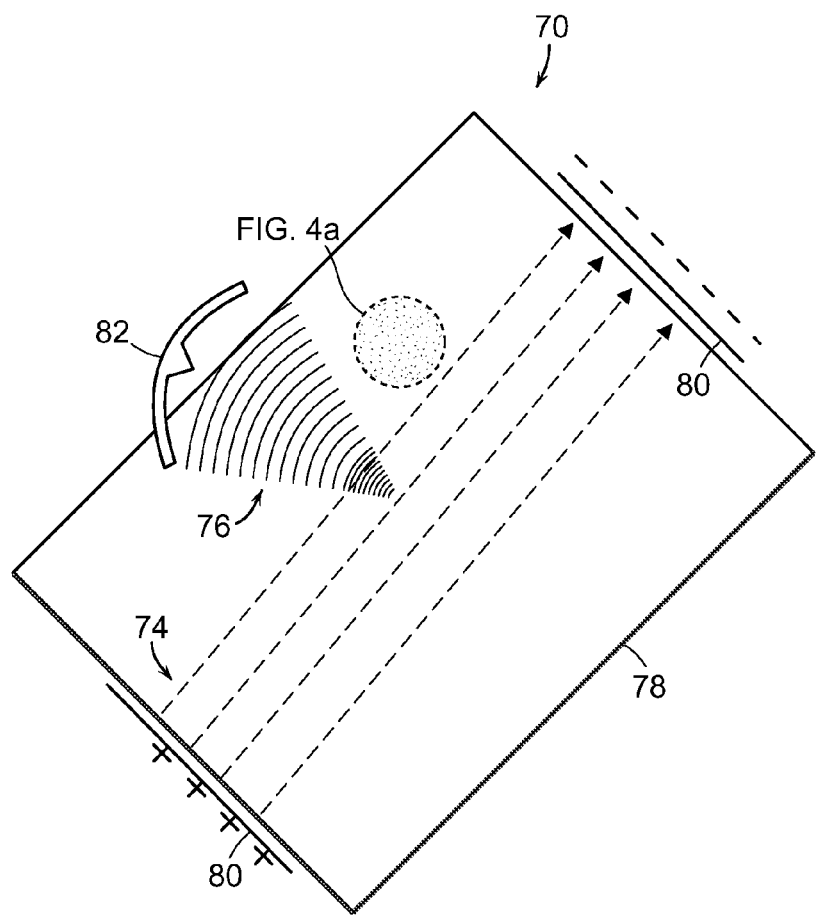
FIG. 4 is a top plan view of an exemplary embodiment of an apparatus for stimulating biological tissue implementing a radiation source for altering permittivity constructed in accordance with the principles of the present disclosure.
Figure 4A:
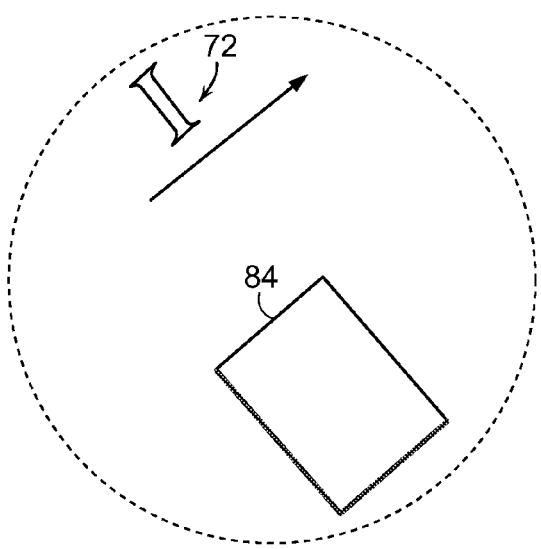

Another example is shown in FIG. 4, which illustrates a set up 70 for applying a method for generating an altered current with a newly generated displacement current 72 through the combined effects of a low frequency electric field 74 and an electromagnetic radiation field 76. A tissue or composite of tissues 78 is placed within a low frequency electric field 74 which is generated by an electric source 80 and combined with radiation source 82 which generates a radiation field 76 that can be focused on the tissue 78. In the area that the radiation field 76 is focused in the tissue 78, the electric field 74 transects the sub component of tissue 84, where the radiation field 76 interacts with the sub component of tissue 84 to alter the tissue's relative permittivity relative to the applied electric field 74, and as such generates a displacement current 72 in addition to the current that would be present due to the source electric field 74 or the radiation source field 76 alone. The electromagnetic radiation field 76 could, for example, interact with the tissue 84 by altering its temperature through ohmic processes, alter the distribution of ions in the cellular and extra-cellular media for instance along ionic double layers along cell walls through the electric forces acting on the ions, or alter the conformation of proteins and other charged components within the tissue through the electric forces such that the permittivity of the tissue is altered relative to the low frequency electric field 74. Furthermore, the electromagnetic field 76, could interact with the tissue 84 by moving components of the tissue via electrorestrictive forces, as would be seen in anisotropic tissues, to alter the continuum permittivity of the tissue relative to the low frequency electric field 74. In addition to the main permittivity change that occurs in the tissues, a conductivity change could also occur in the tissue, which secondarily alters the ohmic component of the currents.

Figure 5:
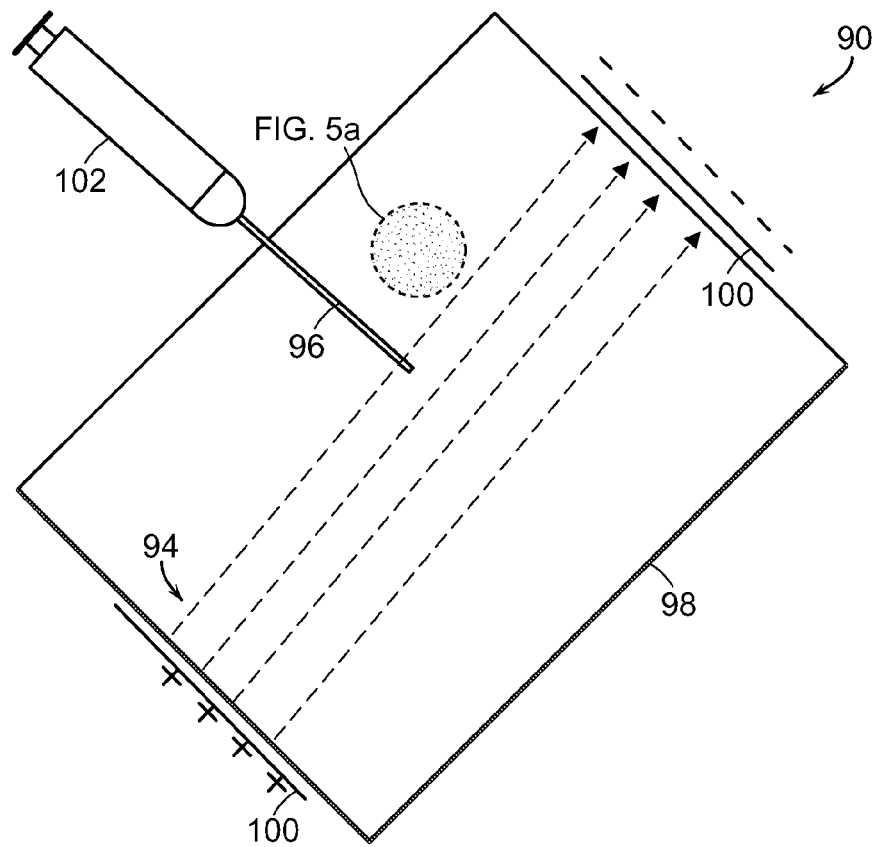
FIG. 5 is a top plan view of another exemplary embodiment of an apparatus for stimulating biological tissue implementing an optical beam for altering permittivity constructed in accordance with the principles of the present disclosure.
Figure 5A:
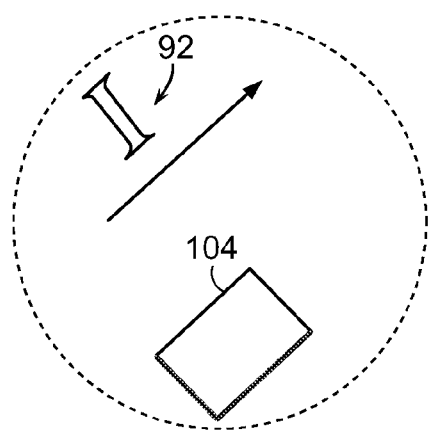

FIG. 5 shows a set up 90 for applying a method for generating an altered current with a newly generated displacement current 92 through the combined effects of an electric field 94 and an optical beam 96. A tissue or composite of tissues 98 is placed within electric field 94 generated by an electric source 100 and combined with optical source 102 which generates optical beam 96 that can be focused on the tissue 98. In the area that the optical beam 96 is focused on the tissue, the electric field 94 transects the sub component of tissue 104, where the optical beam 96 reacts with the tissue to alter the tissue's relative permittivity relative to the applied electric field 94, and as such generates a displacement current 92 in addition to the current that would be present due to the source electric field 94. The optical beam 96 could, for example, interact with the tissue by altering its temperature through photothermal effects and/or particle excitation, alter the distribution of ions in the cellular and extra-cellular media for instance along ionic double layers along cell walls by exciting the movement of ions optically, ionizing the tissue via laser tissue-interactions, or alter the conformation of proteins and other charged components within the tissue such that the permittivity of the tissue is altered relative to the low frequency electric field 94. In addition to the main permittivity change that occurs in the tissues, a conductivity change could also occur in the tissue, which secondarily alters the ohmic component of the currents.

In another embodiment, a thermal source to alter the permittivity of the tissue may be used. In such embodiments, a thermal source such as a heating probe, a cooling probe, or a hybrid probe may be placed external or internal to the tissue to be stimulated. A thermal source may alter the permittivity of the tissue through the direct permittivity dependence of tissue temperature, mechanical expansion of tissues in response to temperature changes, or by mechanical forces that arise due to altered particle and ionic agitation in response to the temperature alteration such that permittivity of the tissue is altered relative to an applied electric field. In addition to the main permittivity change that occurs in the tissues, a conductivity change could also occur in the tissue, which secondarily alters the ohmic component of the currents. This embodiment may be useful for stimulation in the presence of an acute injury to the tissue where the thermal source could be used to additionally assist in the treatment of the tissue injury, for example with a traumatic brain injury or an infarct in any organ such as the heart. The tissue could be cooled or heated at the same time stimulation is provided to reduce the impact of an injury.

In a further embodiment, the method according to the present disclosure is applied in the area of muscular stimulation, where amplified, focused, direction altered, and/or attenuated currents could be used to alter muscular activity via direct stimulation, depolarizing muscular cells, hyperpolarizing muscular cells, modifying membrane potentials, and/or increasing or decreasing the excitability of the muscle cells. This alteration of excitability or firing patterns can last past the duration of stimulation and thus be used as a basis to provide lasting treatment. Additionally, the stimulation can be provided in multiple, but separate sessions to have a summed, or carry-over effect, on the excitability of cells and tissue. Additionally, the stimulation could be provided to prime the tissue by adjusting the muscle cell excitability to make it more or less susceptible to alternate follow up forms of stimulation. The stimulation could be used after another form of stimulation was used to prime the tissue. Furthermore, the stimulation could be applied for a chronic period of time. This embodiment may be useful for altering or assisting cardiac pacing or function, assisted breathing, muscle stimulation for rehabilitation, muscle stimulation in the presence of nerve or spinal cord injury to prevent atrophy or assist in movement, or as substitution for physical exercise.

In yet another embodiment, the method according to the present disclosure can be applied the area of physical therapy, where amplified, focused, direction altered, and/or attenuated currents could be used to stimulate blood flow, increase or alter neuromuscular response, limit inflammation, speed the break down of scar tissue, and speed rehabilitation by applying the focus of the current generation to the effected region in need of physical therapy. It is envisioned that the method according to the present disclosure may have a wide variety in the area of physical therapy including the treatment or rehabilitation of traumatic injuries, sports injuries, surgical rehabilitation, occupational therapy, and assisted rehabilitation following neural or muscular injury. For instance, following an injury to a joint or muscle, there is often increased inflammation and scar tissue in the region and decreased neural and muscular response. Typically, ultrasound is provided to the affected region to increase blood flow to the region and increase the metabolic re-absorption of the scar tissue while electrical stimulation is provided separately to the nerves and muscles; however, by providing them together, a person could receive the benefit of each individual effect, but additionally amplified stimulatory and metabolic effects through the altered currents. The other methods for generating altered currents discussed within could also be used to assist in physical therapy via the displacement currents that are generated.

Furthermore, the method according to the present disclosure may be applied to the area of cellular metabolism, where currents could be used to interact with electrically receptive cells or charged membranes to alter the tissue or cellular dynamics. It is envisioned that this embodiment could provide treatment for various diseases where electrically receptive cells respond to the newly generated displacement currents and altered current distribution.

Furthermore, the method according to the present disclosure may be applied to the area of gene therapy. Amplified, focused, direction altered, and/or attenuated currents could be used to interact with electrically receptive cells or receptors within the cell to influence protein transcription processes and alter the genetic content of the cells. The altered current densities in the tissue can interact with the tissue to stimulate this altered gene regulation. Additionally, the displacement currents generated by the method could further be used to assist in drug delivery and/or gene therapy through the altered current influence on the delivery of agents.

In particular embodiments, methods according to the present disclosure may be applied to treat osteoarthritis. Constant and intense signals (e.g., pain signals and/or inflammatory signals) in peripheral structures, such as an inflamed knee joint, produce significant neurochemical and metabolic changes in the area of the injury. Those changes result in a neurologic reorganization within both the spinal cord and brain that equates to a central sensitization, i.e., a tuned response to the pain. Central sensitization causes neurons to respond to stimuli in a more intense fashion or to stimuli that would not normally elicit a response. Thus, the altered brain function and network response results in chronic pain.

Figure 6:
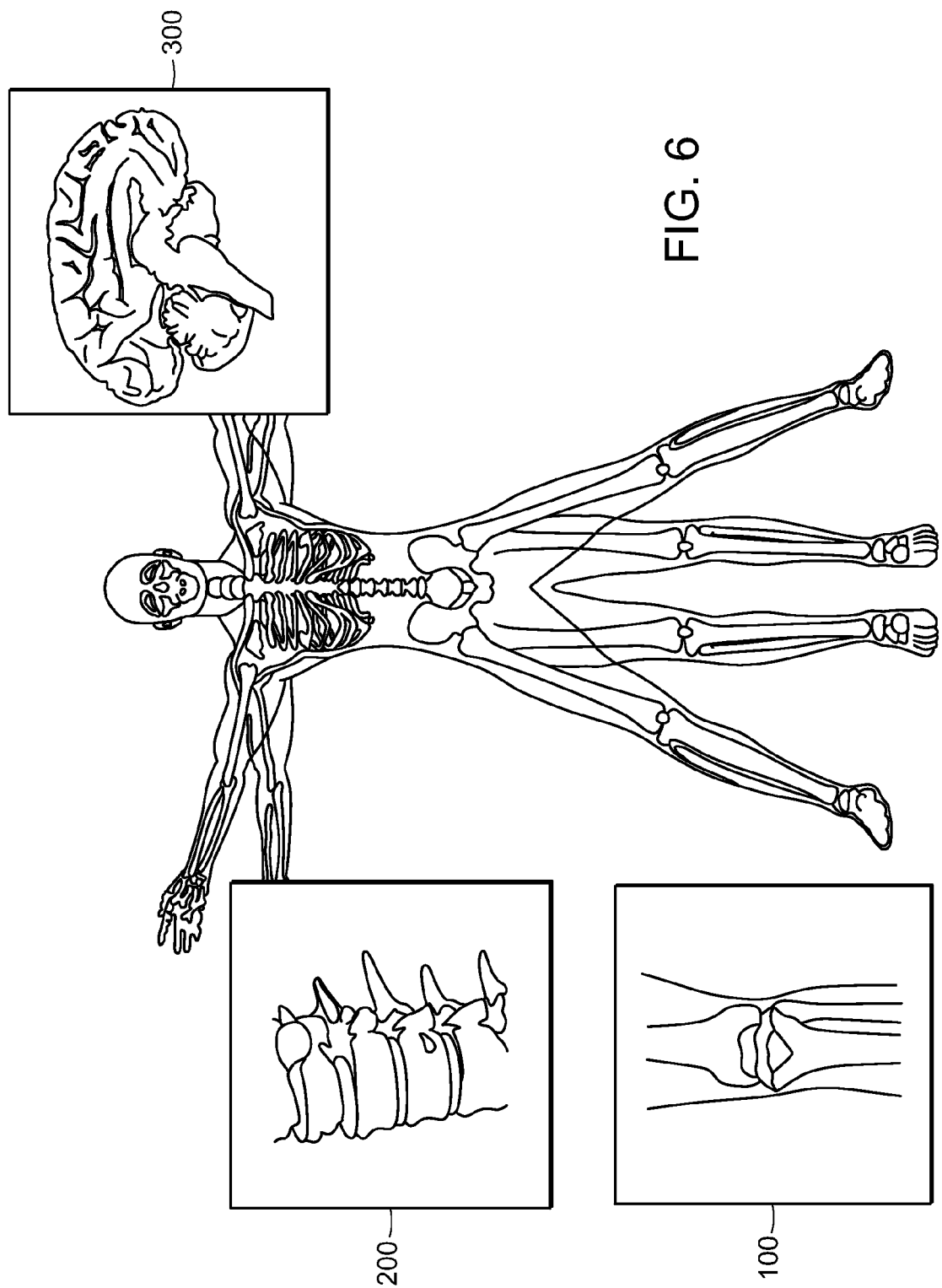
FIG. 6 is a schematic showing the mechanism of action of osteoarthritic pain.

FIG. 6 shows an example of this pain loop involving an osteoarthritic knee. Box 100 shows that a chronic pain signal from an injured joint leads to peripheral pain receptors becoming sensitized to an injury. Box 200 shows that the chronic pain signal causes changes at the spinal cord that amplify electrical activity and the pain signal that is sent to the brain. Box 300 shows that the amplified pain signal sent to the brain results in increased activity in select regions of the brain, leading to central sensitization, i.e., increased pain perception, and amplified facilitory output from the brain. While the knee joint is used as example, this treatment may work in any such body part suffering from the effects of OA, for example an osteoarthritic joint in the neck or shoulder, or similar OA type chronic injuries (i.e., that is the method could be expanded for treatment for any form of arthritis, impingement disorder, overuse injury, entrapment disorder, inflammatory disorder, and/or any muscle, neural, skeletal, or connective tissue disorder which leads to chronic pain, central sensitization, and/or a inflammatory response). For example, one could be suffering from pain from carpal tunnel syndrome from office work, back and neck pain from poor posture during repeated and/or prolonged activities (e.g., sitting in a forced position while driving or during office work), or an athlete could have a chronically inflamed and painful joint from overuse (such as for example a pitchers shoulder being irritated from too much use, or a tennis player suffering from tennis elbow). As a further example, a patient might be suffering from chronic pain in the joints from a gout attack, such as an inflamed toe. As another example, a patient might have a herniated disc, where the damaged disk leads to the nerve being trapped (or even pressed upon by scar tissue or debris left from the injured disc) and inflammation and scar tissue built up in the area lead to a chronic pain type condition. As another example, an athlete could have a build of scar tissue and other debris floating within and/or attached to an injured joint leading to a chronic pain type condition. As another example, the methods and devices described herein could be used to treat patients suffering from cancer related pain (for example bone pain from bone cancer, or pain as a side effect from prolonged cancer treatments (such as for example from secondary pain following long chemotherapy regimens for breast cancer), where the pathology and/or treatment leads to chronic pain, central sensitization, and/or a inflammatory response.

Methods of the invention focus stimulation in select regions of the brain or central nervous system to block processing of pain signals received by the brain from an injured joint. In this manner, methods of the invention prevent or disrupt central sensitization of the pain signal in a person's brain and provide effective therapeutic relief from the pain signal sent from OA damaged joints. Further, elimination of the pain signal breaks the cyclic feedback loop between the injured joint and the brain and leads to reduction in inflammation of the injured joint, thereby treating osteoarthritis.

Any type of stimulation known in the art may be used with methods of the invention, and the stimulation may be provided in any clinically acceptable manner. For example, the stimulation may be provided invasively or noninvasively. Preferably, the stimulation is provided in a noninvasive manner. For example, electrodes may be configured to be applied to the specified tissue, tissues, or adjacent tissues. As one alternative, the electric source may be implanted inside the specified tissue, tissues, or adjacent tissues.

Exemplary types of stimulation include mechanical, optical, electromagnetic, thermal, or a combination thereof. In particular embodiments, the stimulation is a mechanical field (i.e., acoustic field), such as that produced by an ultrasound device. In other embodiments, the stimulation is an electrical field. In other embodiments, the stimulation is an magnetic field. Other exemplary types of stimulation include Transcranial Direct Current Stimulation (TDCS), Transcranial Ultrasound (TUS)/Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). Other exemplary types include implant methods such as deep brain stimulation (DBS), microstimulation, spinal cord stimulation (SCS), and vagal nerve stimulation (VNS). In other embodiments, the stimulation source may work in part through the alteration of the nervous tissue electromagnetic properties, where stimulation occurs from an electric source capable of generating an electric field across a region of tissue and a means for altering the permittivity of tissue relative to the electric field, whereby the alteration of the tissue permittivity relative to the electric field generates a displacement current in the tissue. The means for altering the permittivity may include a chemical source, optical source, mechanical source, thermal source, or electromagnetic source.

In other embodiments, the stimulation is provided by a combination of an electric field and a mechanical field. The electric field may be pulsed, time varying, pulsed a plurality of time with each pulse being for a different length of time, or time invariant. Generally, the electric source is current that has a frequency from about DC to approximately 100,000 Hz. The mechanical field may be pulsed, time varying, or pulsed a plurality of time with each pulse being for a different length of time. In certain embodiments, the electric field is a DC electric field.

In other embodiments, the stimulation is a combination of Transcranial Ultrasound (TUS) and Transcranial Direct Current Stimulation (TDCS). Such a combination allows for focality (ability to place stimulation at fixed locations); depth (ability to selectively reach deep regions of the brain); persistence (ability to maintain stimulation effect after treatment ends); and potentiation (ability to stimulate with lower levels of energy than required by TDCS alone to achieve a clinical effect).

In certain embodiments, methods of the invention focus stimulation on particular structures in the brain that are associated with arthritic pain, such as the somatosensory cortex, the cingulated cortex, the thalamus, and the amygdala. Other structures that may be the focus of stimulation include the basal ganglia, the nucleus accumbens, the gastric nuclei, the brainstem, the inferior colliculus, the superior colliculus, the periaqueductal gray, the primary motor cortex, the supplementary motor cortex, the occipital lobe, Brodmann areas 1-48, the primary sensory cortex, the primary visual cortex, the primary auditory cortex, the hippocampus, the cochlea, the cranial nerves, the cerebellum, the frontal lobe, the occipital lobe, the temporal lobe, the parietal lobe, the sub-cortical structures, and the spinal cord.

In certain embodiments, stimulation may be given well past the period where the injury to the joint is present. For instance, when an artificial joint is implanted in place of an arthritic joint, the chronic pain signal and/sensitization signal can still be present in the brain, and thus stimulation could be used to improve a patient's recovery time following a joint replacement. Thus, stimulation of the central nervous system could have benefits prior to and post surgery for the treatment of injured joints.

In certain embodiments a medical imaging modality may be combined with stimulation. Exemplary imaging modalities include magnetic resonance imaging (MRI), functional MRI (fMRI), ultrasound, positron emission tomography (PET), single photon emission computed tomography (SPECT), computer aided tomography scan (CAT-scan), XRAY, optical coherence tomography (OCT), diffusion tensor imaging (DTI), diffusion spectrum imaging (DSI), electro-acoustic imaging, electromagnetic based imaging, electro-encephalogram (EEG), electromyogram (EMG), high density EEG, spectroscopy based methods, electrocardiogram (EKG) electrical based imaging, magnetic based imaging, nuclear based imaging, optical (photonic) based imaging, mechanical based imaging, thermal based imaging, combined imaging modalities, imaging with contrast agents, imaging without contrast agents, etc. In other embodiments, physiological measurements, stimulation subject assessment measures, and/or biofeedback measures are combined with stimulation.

The imaging modalities, physiological measurements, stimulation subject assessment measures, and/or biofeedback measures could be used to assist in the stimulation by aiding in the targeting (localizing) of stimulation, dosing of stimulation, characterizing safety parameters, analyzing the online or offline effects of stimulation, and/or maximizing the therapeutic effect of stimulation. This facilitation could also be done by altering or controlling the stimulation source(s), field parameters, and/or the stimulation interface apparatus parameters.

In terms of targeting tissues to stimulate, the targeted region can be imaged with any imaging modality that provides anatomical information about the region. That image could then be used to determine the placement of the stimulation source. For example, with an electrosonic (electrical source and mechanical (i.e., sonic/ultrasound), note electrosonic is used synonymously with electromechanical herein) approach one would determine the placement of the electrical source and the ultrasound source to target the desired regions, either directly or within an interface apparatus.

The imaging information could also be used to provide guidance for the design and property tuning of an interface apparatus between the subject to be stimulated and the stimulation source(s). For example, one might simply determine the placement of the source(s) of stimulation and/or the properties of the interface apparatus between the stimulation patient and the device (such as for example the dimensions, materials impedances, and/or design criteria) based on anatomical landmarks determined from the image and predetermined source characteristics (such as for example the beam profile of an ultrasonic transducer and the predicted field distribution of an electric field source).

Additionally, the implementation of an imaging system for targeting could also be used to direct the source fields necessary for stimulation based on calculations developed from the imaging information (or to calculate the field to correlate to stimulation effects following stimulation) and/or physiological measurements, stimulation subject assessment measures, and/or biofeedback measures. An imaging modality could be used to identify the tissue distribution of the subject to be stimulated, from which tissue boundaries in the stimulation area can be identified. This tissue and/or boundary identification could be pursued with any image analysis algorithm, and could be completed prior to stimulation, during stimulation, or following stimulation.

Once the tissues are identified, a 'computational mesh' can be built to capture the tissue segmentation demonstrated in the images, where mesh components can be assigned any physical and/or chemical characteristic of which will be used in determining targeting and localization of the fields, chemicals, and/or stimulation effects (e.g., material properties, electromagnetic properties, thermodynamic properties, mechanical/acoustic properties, optical properties, chemical properties, etc). These properties could be assigned known values determined before stimulation, with values determined during stimulation, or with values determined following stimulation.

Following the generation of a computational mesh based on the tissue properties (and geometry) to be modeled, models can be generated with computational/numerical solvers that capture the physics and/or chemistry of the underlying system such as by also including the source and/or interface properties (position, size, shape, and/or material properties) and/or source field characteristics (amplitude, waveform (shape/timing dynamics), frequency (power components and/or pulse frequencies if using pulsed field), and/or timing information) and/or chemical agent characteristics (concentrations, distributions, compositions, kinetics, and/or additional information).

This can be used to determine the driving field's focus, orientation, focality, and overall distribution in the tissues to be stimulated (such as for example one could determine the electrical field, voltage, current density, magnetic field, force field, mechanical field (acoustic field), pressure field, tissue acceleration, tissue position, tissue velocity, tissue temperature, etc) or the chemical reactions and/or chemistry effects that are modeled (kinetics, chemical distributions, reactions, etc) in the tissue(s) to be stimulated. For a method where tissue properties are modified relative to an applied electric field to generate a new current, this information could then be used to calculate the altered tissue electromagnetic properties (and/or relative positions) relative to the applied electrical field in the tissue(s) to be stimulated, such that one can calculate the newly generated current density and/or electrical field distributions (such calculations can be made with any particular means for altering the tissue electromagnetic properties (including but not limited to mechanical, thermal, electromagnetic, and optical means) in the tissue(s) to be stimulated. Additionally, this information could also be used to guide the placement, design, material properties, and/or modification of an interface mechanism.

Ultimately this can allow for pre, during, or post stimulation targeting/localization via calculations based on the initial imaging modality, tissue characteristics, field source characteristics, and/or the properties of the interface apparatus (and/or the source characteristics of the means that alters the electromagnetic properties of the tissue to be stimulated from combined methods where new currents are generated relative to an electric field source). These methods could be implemented with any form of stimulation, including but not limited to electromagnetic, mechanical (i.e., acoustic), optical, thermal, electrical, magnetic, and/or combined methods (and/or methods which alter tissue impedances relative to electrical sources to generate altered stimulation currents, for example with electromagnetic, mechanical (i.e., acoustic), optical, thermal, electrical, magnetic, and/or combined sources).

In one particular example, in the area of brain stimulation, with an electrical source generating an applied electrical field and/or ultrasound (i.e, mechanical) source generating focused acoustic energy on the tissue area to be stimulated, the electrical field distribution and/or the mechanical field distribution can be calculated based on the relative electrical field and mechanical field transducer source characteristics (transducer position(s), transducer size(s), transducer shape(s), field frequencies, field time dynamics, field amplitudes, field phase information, etc) to anatomical tissue distribution (with the appropriate tissue characteristics (for example the electromagnetic properties and tissue mechanical/acoustic properties)) which can be determined from any imaging methodology which provides anatomical information about the area to be stimulated (such as for example a CAT-scan or and MRI) and/or with predetermined tissue characteristics (and/or also with values which at least in part could be determined via an imaging modality, such as conductivity characteristics based on DTI images); for example one might solve a modified Laplacian, $$\nabla \cdot \left( \frac{\partial (\varepsilon \nabla \Phi)}{\partial t} + \sigma \nabla \Phi \right) = 0,$$

for the an electrical potential (where $\Phi$ is solved in the sinusoidal steady state for particular angular frequency, $\omega$, of the electrical source for particular permittivities, $\in$, and conductivities, $\sigma$, of the tissues being examined (as functions of the frequency of the stimulation electrical field)) based on a particular electrical source, and the Westervelt equation:

$$\nabla^2 p - \frac{1}{c^2} \frac{\partial^2 p}{\partial t^2} + \frac{\delta}{c^4} \frac{\partial^3 p}{\partial t^3} + \frac{\beta}{\rho c^4} \left[ p \frac{\partial^2 p}{\partial t^2} + \left( \frac{\partial p}{\partial t} \right)^2 \right] - \nabla p \cdot \nabla (\ln p) = 0$$

for a particular mechanical source (where p is pressure, and c is the speed of sound, $\delta$ is acoustic diffusivity, $\beta$ is the coefficient of nonlinearity, and $\rho$ is the density of the respective tissues), and the appropriate boundary conditions between varied tissues. The calculated electrical and mechanical field distributions can be used to calculate the altered tissue electromagnetic properties (and/or relative tissue positions (with varied tissue electromagnetic properties)) relative to the applied electrical field, such that one can calculate the newly generated current density and/or electrical field distributions; for example one could pursue tissue/field perturbation model and/or a hybrid Hinch/Fixman (Chew; Fixman 1980; Chew and Sen 1982; Fixman 1982; Hinch, Sherwood et al. 1983) inspired model of dielectric enhancement to determine field perturbations and changes in bulk permittivity, thus ultimately calculating the current density distributions in the brain during stimulation (where $J=\sigma E+\partial(\in E)/\partial t$, J is the current in the tissue, $\sigma$ the tissue conductivity, E the total field (i.e., source plus perturbation field), and $\in$ is the tissue permittivity; in regions outside of the main focus fields could be determined through continuity equations).

This information will in turn allow one to predict the distribution of the fields and/or currents in the brain based on the imaging and stimulation source information and thus predict locations of effect of stimulation (and/or magnitude of effect). If one chose to use an interface apparatus during the stimulation, such as a helmet like mechanism, the helmet itself could be tailored uniquely for a subject being stimulated based on the calculated field and/or targeting information (such as where one could integrate the helmet design and materials into all of the subsequent physics (and chemical) based calculations). This information and/or resulting calculations could also be integrated with physiological measurements, stimulation subject assessment measures, and/or biofeedback measures, as it could be used to assist in the stimulation by aiding in the targeting (localizing) of stimulation, dosing of stimulation, characterizing safety parameters, and/or analyzing the online or offline effects of stimulation. This facilitation can also be done by altering or controlling the stimulation source(s), field parameters, and/or the stimulation interface apparatus parameters (based on the calculations and/or other feedback information).

One could implement a closed loop system which could automatically tune stimulation based on the calculations and/or feedback which is gathered and fed into an automated control system(s) to tune stimulation results to a desired response based on a particular algorithm and/or an adaptive system; one could implement a system which allows a person or persons operating the stimulation system to modify the stimulation system itself to achieve a desired response relative to the information/feedback that is gathered; and/or a hybrid system of control (note that the information/feedback can be gained from any imaging modalities, biofeedback, physiological measures, and/or other measures as exemplified above). Accordingly, these methods could be implemented with any stimulation method by adapting the physical field calculations appropriately (for example electrical field sources and effects could be calculated with the modified Laplacian equation or TUS acoustic fields could be solved with the Westervelt equation alone (one could also calculate local field changes based on sources of electrical fields such charged proteins, membranes, and macromolecules, similar to the methods outlined above).

These methods could be implemented with any form of stimulation. Exemplary types of stimulation include mechanical, optical, electromagnetic, thermal, or a combination thereof. In particular embodiments, the stimulation is a mechanical field (i.e., acoustic field), such as that produced by an ultrasound device. In other embodiments, the stimulation is an electrical field. In other embodiments, the stimulation is a magnetic field. Other exemplary types of stimulation include Transcranial Direct Current Stimulation (TDCS), Transcranial Ultrasound (TUS)/Transcranial Doppler Ultrasound (TDUS), Transcranial Electrical Stimulation (TES), Transcranial Alternating Current Stimulation (TACS), Cranial Electrical Stimulation (CES), or Transcranial Magnetic Stimulation (TMS). Other exemplary types include implant methods such as deep brain stimulation (DBS), microstimulation, spinal cord stimulation (SCS), and vagal nerve stimulation (VNS). In other embodiments, the stimulation source may work in part through the alteration of the nervous tissue electromagnetic properties, where stimulation occurs from an electric source capable of generating an electric field across a region of tissue and a means for altering the permittivity of tissue relative to the electric field, whereby the alteration of the tissue permittivity relative to the electric field generates a displacement current in the tissue. The means for altering the permittivity may include a chemical source, optical source, mechanical source, thermal source, or electromagnetic source.

Stimulation targeting, localization, and/or field information could also be integrated with additional technologies. For instance, one could integrate the imaging based field solver methodologies with frameless stereotactic systems to track/target stimulation location during a procedure. Additionally, as this targeting, localization, and/or field information can be used to predict the strength and orientation of the current densities (and/or other fields) generated in the tissues relative to the tissue to be stimulated, this information can in turn be fed into neural modeling algorithms (such as Hodgkin and Huxley based stimulation models) that can be used to predict the neural response and/or the information can be used to guide dosing of stimulation. Additionally, the information could be used to adjust the parameters of stimulation and or the characteristics of the interface.

Imaging modalities, physiological measurements, stimulation subject assessment measures, and/or biofeedback measures can also be used to track the effect of stimulation, and ultimately be integrated with the stimulator and/or a interface apparatus to provide a closed loop system of controlled stimulation (and/or with the targeting/field information described above). Imaging modalities that provide information such as but not limited to tissue electrical activity (such as for example, EEG data from the brain for neural stimulation or EKG information from the heart for cardiac stimulation or EMG data from muscle during neural and/or muscle stimulation or electro-retinal gram (ERG) data for visual system stimulation), tissue metabolic information (such as from glucose information from a fluorodeoxyglucose (FDG) based PET scan), tissue blood flow/absorption (such as blood flow information that might be determined from a BOLD signal that might be determined during MRI or with modified functional measures), neuroreceptor activation (such as through radioligands that bind to dopamine receptors and can be imaged with modalities such as PET), tissue temperature changes (such as from thermal imaging), and/or any information of tissue response could be integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation. Such imaging modalities, used to track the effect of stimulation, could also be integrated with methods elaborated on above to assist in targeting and dosing calculations.

Similarly physiological measurements such as but not limited to heart rate, respiratory rate, blood gas levels, blood pressure, respiratory gas compositions, urine and fluid concentrations, blood chemistry (including hormone levels), electrolyte levels, pain markers, stress indicators, joint function measures (e,g, mobility, strength, range of motion), patient weight, sensory markers, auditory measures, perceptual measures, emotional markers, skin conductance (i.e., sweat level), pupil dilation, emotional markers, temperature, fluid levels, body/limb position, fatigue markers, fear markers, coordination measures, psychiatric markers, addiction markers, motor performance measures, and/or eye position/movement could be also integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation.

Such physiological measurements, used to track the effect of stimulation, could also be integrated with methods elaborated on above to assist in targeting and dosing calculations. Additionally, one could use other biofeedback or stimulation subject assessment information directly gathered from the subject being stimulated such as but not limited to task performance (such as a motor performance, memory, or learning task), subject response (such as to depression based questionnaire/metrics to assess mood), pain measures (such as pain assessment levels or amount of pain killers used), addiction measures (such as alcohol consumption or drug use), subject gathered reports, subject based observations, and/or any subject based self assessments could be also integrated with the stimulation method to provide system based feedback and provide guidance to hone stimulation field parameters such as the stimulation duration, stimulation waveform shape (amplitude and dynamics); source position, size, shape relative to tissues to be stimulated; and/or stimulation targeting, localization, and/or field parameters, such as the source fields timing dynamics, amplitude and orientation. Such measures, used to track the effect of stimulation, can also be integrated with methods elaborated on above to assist in targeting and dosing calculations.

One could tune/adjust such things as the stimulation source(s) position(s), size(s), and/or shape(s) relative to the tissue to be stimulated (such as the electrodes for generating the electric fields, transducers for generating acoustic fields, and/or the source of the means for modifying the electromagnetic parameters of tissues to be stimulated (i.e., mechanical/acoustic field source/transducer, optical source, thermal source, chemical source, and/or a secondary electromagnetic field source)); the field(s) that are generated from sources in terms of magnitude, direction, waveform dynamics, frequency characteristics (power spectrum of waveform and/or potential pulse frequency of stimulation field waveforms), phase information, and/or the duration of application; and/or chemical processes (duration, kinetics, chemical concentrations, distributions, etc) driven by sources.

Additionally, imaging modalities, physiological measures, biofeedback measures, stimulation subject assessments, and/or other measures might not just be integrated with the process that stimulates tissues through the combined application of electrical and/or mechanical fields (and/or chemical agents, thermal fields, optical fields/beams, and/or secondary electromagnetic fields), but effectively they could also be integrated with an interfacing apparatus to increase the interface apparatus's efficiency or modify its use relative to the measures outlined above such as but not limited to altering the material properties of the interface (such as for example altering the electrical impedance of a component(s) of the interface or altering a mechanical/acoustic properties of a component(s) of the interface mechanism such as the acoustic impendence); alter the interface apparatus position, size, shape, and/or position; alter the components of the stimulation process that it stores or interfaces with (such as in size, shape, and/or position; for example the source of the electric field and/or means to alter the tissue electromagnetic properties for tissue stimulation); altering composition(s) of the material(s) within and/or on the interface (such as fluid concentrations to couple a mechanical source with tissues to be stimulated); to control the number of uses of the interface (or the duration of its use); and/or any adjustable quality as described above in the interface description.

These modifications can be made before a stimulation session (based on previously obtained/analyzed information), during stimulation (with real time or online information), or following stimulation for subsequent stimulation sessions (with data analyzed following stimulation). One could also adjust/tune the stimulation parameters based on the information acquired before stimulation not compared to anything, during stimulation (online) compared to the pre-stimulation baseline, inter-stimulation session comparisons, cross stimulation session comparisons, pre vs. post stimulation comparisons, across multiple samples (such as across patient populations with averaged data), and/or any combination or permutation in which the data is obtained and/or analyzed. These methods could be implemented with any form of stimulation, including but not limited to electromagnetic, acoustic, optical, thermal, electrical, magnetic, and/or combined methods (and/or methods which alter tissue impedances relative to electrical sources to generate altered stimulation currents, for example with electromagnetic, acoustic, optical, thermal, electrical, magnetic, and/or combined sources).

One could implement a closed loop system which could automatically tune stimulation based on the information/feedback which is gathered and fed into an automated control system(s) to tune stimulation results to a desired response based on a particular algorithm and/or an adaptive system; one could implement a system which allows a person or persons operating the stimulation system to modify the stimulation system itself to achieve a desired response relative to the information/feedback that is gathered; and/or a hybrid system of control (note that the information/feedback can be gained from any imaging modalities, biofeedback, physiological measures, and/or other measures as exemplified above).

For example in the area of brain stimulation, with an electromechanical (i.e., electrosonic) based stimulator, with an electrical source providing a primary electric field and an acoustic source providing focused acoustic energy, one could set up a system such that source electrodes for generating the primary electric field can have their size, shape, and/or position modified in real time as directed by imaging information (and/or any other type of information) that is being gathered during stimulation. Similarly, one could set up a system such that a source transducer for generating an acoustic field can have its shape (and/or size) modified in real time and/or have its position changed in real time as guided by imaging information (and/or any other type of information) that is being gathered during stimulation.

Similarly the fields that are generated by these sources can have their amplitude, waveform dynamics/timing, frequency characteristics, phase characteristics, distribution, duration, direction, and/or orientation altered as directed by imaging information (and/or any other type of information) that is being gathered before, during, or after stimulation. Similarly if an interface apparatus is being used, it could have any of characteristics altered (size, shape, position, material properties, source contained positions (sizes and/or shapes), etc), such as for example part of its electrical impedance altered such that an electrical field that is targeting underlying tissue could be redirected to another tissue location as guided by imaging information (and/or any other type of information) that is being gathered during stimulation. For example, one could provide electromechanical stimulation (electrical field combined with a mechanical field) to a subject's brain while simultaneously recording the EEG response, and subsequently use the EEG imaging information as a guide to neural response to guide an algorithm which controls the alteration the electromechanical stimulation parameters (for example the source position, field amplitudes, stimulation waveform, stimulation duration, etc) of the electrical and mechanical field sources to tune the desired EEG response (For example one could analyze the power and/or frequency information in the EEG signal relative to stimulation provided, and in turn adjust the stimulation parameters relative to the EEG signal (such as for example, the amplitude and/or frequency properties of the mechanical and electrical source generated fields could be adjusted relative to the real time EEG response).

Or for example, one could adjust the location of the source positions along a stimulation subject's scalp, based on field calculations made as explained above, but additionally tuned with functional MRI (fMRI) information depicting location effects of stimulation, and further integrated with real time EEG data). The stimulation parameters could simply be modified by a person administering the stimulation, or be automatically controlled through a computer/machine based feedback control system during stimulation (essentially making a closed loop system), and/or a hybrid system of control. Or furthermore, the interface between the electrical field source and/or the acoustic field source could be modified through the controlled feedback system to aid in targeting or to optimae the therapeutic effect of stimulation.

Additionally, imaging modalities, physiological measures, biofeedback measures, stimulation subject assessments, and/or other measures might also be used to monitor safety parameters in the tissue before, during, and/or after stimulation (either via calculations based on the imaging and source information, and/or measured information alone).

For instance one could use the thermal information to assure tissue temperatures remain within desired levels, electrical activity information to assess for potential seizure activity or abnormal neural response, current density magnitude calculations in the tissue (including a breakdown of the current types (i.e., ohmic vs. capacitive)) to determine if stimulation currents are within appropriate safety windows, psychological measures from a stimulation subject response (such as for example markers for depression and/or mood) to determine if stimulation is having the appropriate psychological response, physiological measures from a stimulation subject (such as for example heart rate and other system measures) to determine if stimulation parameters are being applied safely, and/or other various safety markers.

These different methods can all be combined together in whole or in part and used to tune and/or alter the stimulation source characteristics, field parameters, calculated fields, the interface apparatus characteristics, and/or other qualities at any point before, during, or after stimulation to aid in the targeting (localizing) of stimulation, dosing of stimulation, characterizing safety parameters, and/or analyzing the online or offline effects of stimulation.

And furthermore, such imaging, biofeedback, physiological measurement, and other modalities in conjunction with the altered current generation could similarly be applied in the areas of altering cellular metabolism, physical therapy, drug delivery, and gene therapy as explained in the referenced patent application (U.S. patent application Ser. No. 11/764,468, Apparatus and Method for Stimulation of Biological Tissue) and above as focused on treating OA. These examples are provided not to be exhaustive, but as an example of potential applications.

All of the methods and processes discussed in this document could be implemented with any form of stimulation, including but not limited to electromagnetic, acoustic, optical, thermal, electrical, magnetic, and/or combined methods (and/or methods which alter tissue impedances relative to electrical sources to generate altered stimulation currents, for example with electromagnetic, chemical, acoustic, optical, thermal, electrical, magnetic, and/or combined sources).

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein.

EXAMPLES

Figure 7:
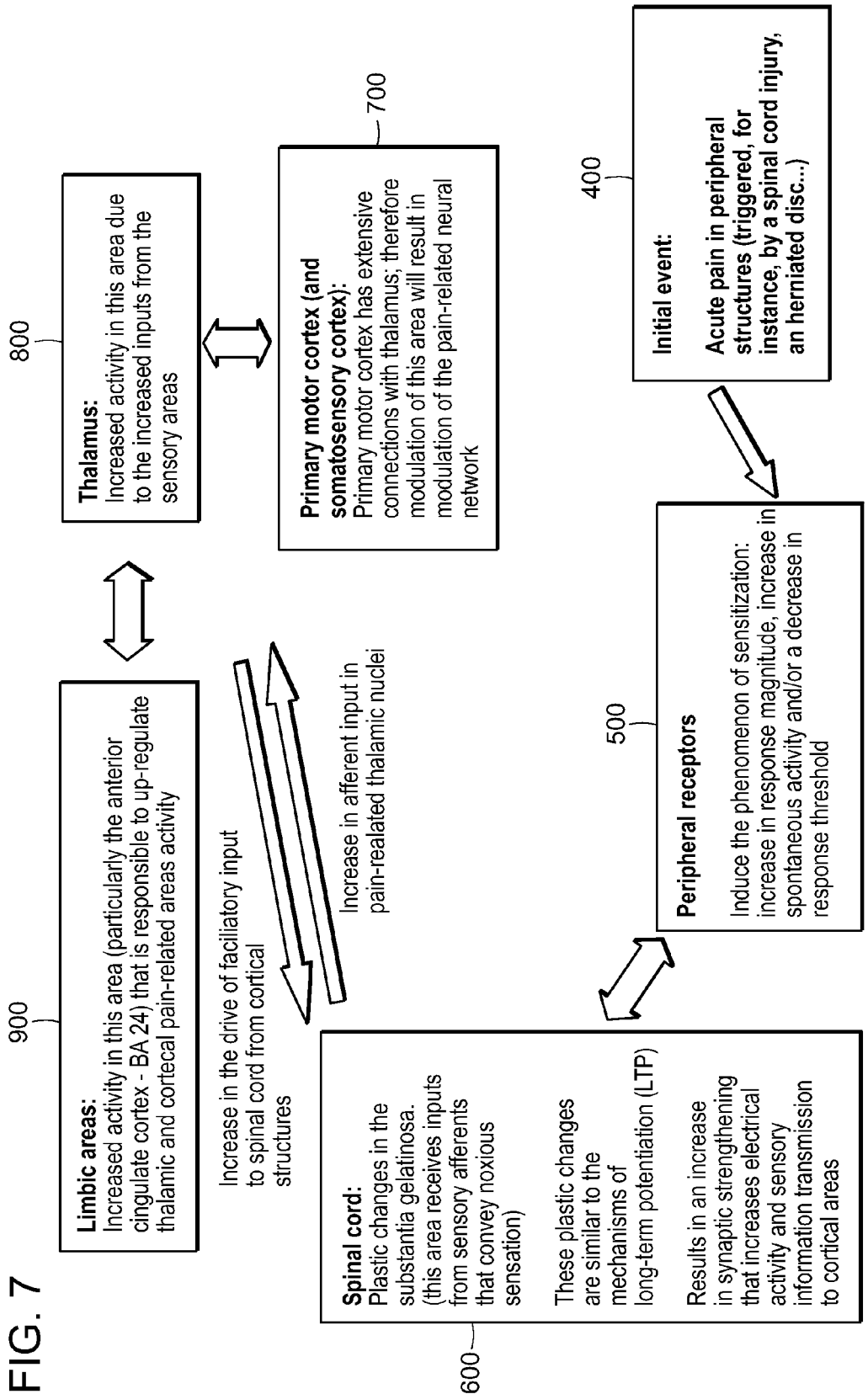
FIG. 7 is a flow diagram showing the phenomenon of central sensitization.

An example of the central sensitization in chronic pain can take place is shown in FIG. 7. Box 400 shows that an initial event, such as spinal cord injury, herniated disc, a traumatic injury to a joint, results in acute pain peripheral structures. The acute pain effects peripheral receptors that induce the phenomenon of sensitization, which results in an increase in response magnitude, increase in spontaneous activity, and/or decrease in response threshold in the periphery (Box 500). This triggers changes in the spinal cord, such as plastic changes in the substantia gelatinosa (this area receives inputs from sensory afferents that convey noxious sensation) (Box 500). The plastic changes are similar to the mechanisms of long-term potentiation, which results in an increase in synaptic strengthening that increases electrical activity and sensory information transmission to cortical areas. The changes in spinal cord activity send signals to certain brain structures which leads to certain activity in those structures. For example, there is increased activity in the thalamus due to increased inputs from the sensory areas (Box 800). The thalamus then sends signals to the limbic areas (Box 900) and the primary motor cortex and somatosensory cortex (Box 700). There is increased activity in the limbic areas (particularly the anterior cingulated cortex—BA 24) that is responsible to up-regulate thalamic and cortical pain related area activity. Since the primary motor cortex has extensive connections with the thalamus, modulation of the thalamus results in modulation of this pain-related neural network. Note, this is just an example depicting components of the central nervous system that can be involved in the process, it is not all inclusive as many other brain regions can be involved via the pathways depicted herein and additional pathways not indicated in the figure.

This Figure shows that the communication between the thalamus and the limbic area is reciprocal (arrow connecting Boxes 800 and 900) and that the communication between the thalamus and the primary motor cortex is also reciprocal (arrow connecting Boxes 800 and 700). Additionally, the communication between the spinal cord and the brain is reciprocal (arrow connecting Boxes 600 and 800). Thus a cyclic feedback loop is created between the brain and the spinal cord, resulting in the initial signal feeding back on itself can consequently intensify without any additional signal from the initial injury event. Additionally, communication between the spinal cord and the peripheral receptors can be reciprocal (arrow connecting Boxes 500 and 600).

Example 1

Subject Selection 48 chronic osteoarthritis pain subjects will be selected to take part in this study. All subjects should meet the following inclusion and exclusion criteria. The inclusion criteria are: 18 to 64 years old; having chronic osteoarthritis knee pain in the left knee (existing pain for more than 6 months with an average of at least 3 on a 0-10 VAS scale); pain resistant to common analgesics and medications for chronic pain such as Tylenol, Aspirin, Ibuprofen, Soma, Parafon Forte DCS, Zanaflex, and Codeine; and must have the ability to feel pain as self reported.

The exclusion criteria are: patient is pregnant; contraindications to tDCS (e.g. metal in the head or implanted brain medical devices); contraindications to TUS (e.g. metal in the head or implanted brain medical devices); history of alcohol or drug abuse within the past 6 months as self reported; use of Carbamazepine within the past 6 months as self reported; suffering from severe depression (with a score of >30 in the Beck Depression Inventory); history of neurological disorders as self reported; history of unexplained fainting spells as self reported; history of head injury resulting in more than a momentary loss of consciousness as self reported; and history of neurosurgery as self reported.

Example 2

Subject Enrollment

Potential subjects will be identified by the following sources: attending physicians may refer their chronic osteoarthritis pain outpatients to the study or flyers posted in the outpatient specialist clinics. Eligible subjects will contact or give permission to be contacted by a co-investigator to obtain more information about the study and give informed consent. At the first point of contact (usually a phone call), study co-investigator will administer a phone screening questionnaire, which will involve some sensitive medical information (psychiatric, drug and alcohol history as exclusion criteria). Once the phone screening process is complete, the information gathered by the co-investigator will be taken to the principle investigator (PI) of the study for further review. Once the PI agrees that the subject is thus far eligible, the subject will then be reached again to schedule their first visit. Data obtained from screening will be stored in a locked filing cabinet in the lab.

Informed consent will be obtained by an investigator (not involved in the subject's care). The subject will meet with the PI and the co-investigator. The test procedures will be described and the testing equipment will be shown to the subject. A co-investigator will clearly explain all the procedures and risks of the testing outlined in the consent form. The subject will be given an hour to consider their decision and will be encouraged to ask questions, both during the initial interview and throughout the study. The PI or a co-investigator will answer any questions regarding the study at the time consent is given. Once enrolled, the subject may pause or terminate his/her participation at any time during the study.

Example 3

Pre-Screening

During the pre-screening process, the subject will contact the research coordinator of the study by phone. During this call, the coordinator will discuss in greater depth the details of the study. In the privacy of the laboratory, the coordinator will ask the subject questions from the following: phone screening questionnaire and TDCS contraindications checklist Once this information is collected, the coordinator will consult with the principal investigator, who will give final approval for the subject to be part of the screening procedure. During the pre-screening period, informed consent forms will be given to potential subjects for review. The pre-screening process will last duration of approximately half an hour.

Example 4

Chronic Osteoarthritis Pain Subjects

During a first doctor's visit a review of inclusion/exclusion criteria will be conducted to determine the subject's eligibility for enrollment. No stimulation will be applied during this visit. Study procedures will be reviewed with the subject, and documentation of informed consent will be obtained. At Screening the following procedures will be completed: discuss study-specific procedures with the subject; review inclusion and exclusion criteria; review of medical history; obtain a signed and dated consent form; discuss pain/medication diary; and randomization into one of the two study arms, active stimulation or SHAM stimulation.

A baseline evaluation will also be performed at this visit. The following procedures will be completed: VAS pain assessment; VAS anxiety assessment; discuss medication diary; discuss pain diary; quality of Life Assessment; BDI; Von Frey assessment; pain pressure threshold via algometer; descending noxious inhibitory control exam; and transcranial Doppler Exam During visits 2 through 6, patients will receive stimulation sessions. During the stimulation period of the visits subjects will be asked to complete the following during each visit:

VAS pain assessment; VAS anxiety assessment; discuss medication diary; discuss pain diary; quality of life assessment; BDI; Von Frey assessment; pain pressure threshold via algometer; descending noxious inhibitory control exam; adverse effect; sensory testing; side effect questionnaire; and transcranial ultrasound (Doppler exams also pre and post stimulation).

Visits 7-9 will be completed 2, 4, and 8 weeks post stimulation and will assess the pain, anxiety, and medication logs for the week after the last stimulation procedure. The following will be completed during each visit: VAS pain assessment; VAS anxiety assessment; quality of life assessment; medication diary/pain diary; Von Frey assessment; pain pressure threshold via algometer; descending noxious inhibitory control exam; BDI; and transcranial Doppler exam.

Example 5

Experimental Protocol

Subjects will be randomized to undergo one of two different stimulation protocols: five sessions of sham tDCS and ultrasound or five sessions of active anodal tDCS combined with transcranial ultrasound (24 subjects per study arm). Transcranial Doppler ultrasound exams will be made pre and post stimulation following the protocols detailed below (following procedures outlined in (Aaslid et al. J Neurosurg, 57(6): 769-774, 1982), to determine the MCA, PCA, and ACA flow velocities.

Each tDCS and transcranial ultrasound stimulation session will last 20-minutes and will be conducted with a Highland Instruments ESStim Stimulation device using up to 2.0 mA of DC current. The electrodes/transducer that will be used will be standard sponge electrodes and a standard transducer. The anode will be placed over C3/C4 (International 10/20 Electroencephalogram System), which corresponds approximately to the location of the motor cortex. The inactive cathode electrode will be placed over the contralateral orbital.

For sham procedures, the same montage will be used; however current and ultrasound will be applied for less than 30 seconds so that the subject experiences the same sensation of the device turning on the sham subjects (the turning off of the device is not perceived due to sensitization). It should be noted that less than 3 minutes of current induces no lasting effects on cortical excitability (Nitsche et al. J Physiol 527(3):633-639, 2000) and also using 30 seconds of sham is a reliable method of blinding, as shown by a randomized controlled study (Gandiga et al. Clin Neurophysiol 117(4):845-850, 2006). Additionally, an inactive ultrasound transducer will be held in place during the sham stimulation to further ensure blinding.

The schedule for the subjects can be seen in table 1, which illustrates the procedures that will be performed AT each visit. Sensory testing sessions (PPT, VAS, Von Frey, DNIC) will be carried out before, during, and after stimulation.

TABLE 1

Chronic Pain Osteoarthritis Subjects

| Evaluations: | V 1 | V2-V6 | V 7 | V 8 | V 9 |
|---|---|---|---|---|---|
| Consent Process | X | | | | |
| VAS Pain | X | X | X | X | X |
| Quality of Life | X | X | X | X | X |
| BDI | X | X | X | X | X |
| VAS anxiety | X | X | X | X | X |
| Medication Diary | X | X | X | X | X |
| Pain Diary | X | X | X | X | X |
| Pressure-pain threshold (PPT) via Algometer | X | X | X | X | X |
| Von Frey | X | X | X | X | X |
| Descending Noxious Inhibitory Control (DNIC) | X | X | X | X | X |
| Transcranial Doppler Exam | X | X | X | X | X |
| Adverse effect questionnaire | | X | | | |
| tDCS combined with transcranial ultrasound (active or sham) | | X | | | |

The primary efficacy variable will be the change in pain (as indexed by VAS) comparing before and after stimulation assessments. Secondary outcome measures included: number of responders, the percentage of subjects with >50% reduction in the mean pain (VAS) (categorical—responders rate); change in pain pressure threshold using algometer and Von Frey hair; change in the mean number of days of acute medication intake; mean changes from baseline on the Quality of Life Questionnaire (MSQ, Version 2.1); and change in the VAS anxiety.

An additional questionnaire will be used to monitor adverse events. At the end of the session, the subject will describe any sensations they felt during stimulation and anything unexpected that happened during the study visit using the tDCS Side Effects Questionnaire. Doppler flow rates for the MCA, ACA, and PCA will also be acquired and analyzed pre and post stimulation.

Example 6

Sensory Testing

Pressure pain threshold (PPT): PPT will be determined using blunt pressure delivered by a 1-cm$^2$ hard-rubber probe using a FDA approved device (commander algometer—JTECH medical). During testing, a series of discrete pressures are applied to the painful site (i.e., left knee) with the control site being the thenar area (or other non-painful site (i.e., if contralateral knee is pain free it will be used)). The patient will let the investigator know when he/she feels any pain and at that time the procedure will be stopped and the value will be recorded. This procedure will be repeated 3 times. The test will take approximately 7-10 min to complete.

Von Frey hair: Mechanical perception and pain threshold will be tested on the painful region and thenar areas (or other non-painful site) using Von Frey monofilaments (0.4 g to 50 g) (these are fine filaments that can test a subjects perception threshold when they are applied to the body surface). Monofilament application will be at both the left and right sides of the painful region (i.e., left knee) and to the thenar areas both left and right side (or other non-painful site). The hairs will be applied until subject perceives the stimulus (perception threshold) and describes it as painful (pain threshold). The threshold will be taken as the lowest force that causes pain perception in the affected and contralateral mirror healthy site.

Descending Noxious Inhibitory Control (DNIC): Endogenous Pain modulation is commonly evaluated in the laboratory using DNIC testing paradigms. These procedures incorporate a conditioning stimulus (a noxious stimulus that evokes DNIC activation) and a test stimulus (a noxious stimulus used to evaluate the analgesic response to the conditioning stimulus-this will be the PPT). This study will evaluate DNIC in pain patients using pressure as the test stimulus, and cold water as the conditioning stimulus. Pressure will be delivered using the same device as for the evaluation of PPT. DNIC will be induced 5-min later by having subjects immerse their hand into a water bath maintained at 10-12° C. for 1 min. Parallel to the last 30-s of DNIC conditioning (cold water immersion), the same test stimulus will be reapplied (PPT procedure) DNIC will be evaluated as the mean difference in pain rating of the test stimulus applied before and during the conditioning stimulus. This value would typically be treated as a continuous variable if measured repeatedly in a clinical trial because it is unlikely that descending analgesic systems are either "on" or "off", but rather function within a range of magnitudes across subjects.

Questionnaires: All questionnaires will be administered in the privacy of a closed lab. If subjects feel uncomfortable in answering any of the questions they may stop the study at any time.

Example 7

Biostatistical Analysis

The main outcome will be the comparison of mean pain changes immediately before and after stimulation between the anodal and the sham tDCS combined with transcranial ultrasound, as assessed by a paired t-test. We calculated the sample size powered to detect a difference between the anodal and sham based on the results as described in Fenton et al. (Gynecol Obstet Invest, 65(4):247-251, 2008) in which subjects with chronic pain received 2 sessions of tDCS. In this study it was shown that there was a VAS difference between active anodal and sham tDCS of 0.797 (with an SD of 0.5). Using these numbers and assuming a type I error of 5% (alpha), a type 2 error of 10% (beta) and therefore the power will be 90%; the sample size calculation for a normal distributed population (t-test) results in a total of 12 subjects.

However, the clinically meaningful difference between these two groups will be used to calculate the sample size. It was determined that a difference of 2 points in VAS between active and sham would be clinically meaningful. Considering 5% for alpha and 90% for power, the sample size will then be 34 subjects (17 in each arm). Conservatively, it is expect that there will be a 10% rate of dropout or loss to follow-up. It will assume that dropout subjects will not improve from the last measured point; thus the sample size has to be increased by 10% to 38 subjects. In order to account for unexpected factors such as higher placebo response and the possible need for nonparametric tests, the sample size was increased by 20% to 48 subjects.

Statistical analysis (Aim 1): The main outcome of this study is mean pain improvement as measured by a VAS. However, pain improvement will be analyzed using two methods: frequency of pain responders (binary outcome) and mean of pain reduction (continuous outcome). Pain responders will be defined as subjects with a decrease of 50% in VAS. However, in addition, decrease in analgesic use will b e analyze and stimulation will be consider a failure if VAS reductions are seen with increased analgesic use or VAS increases with decreased analgesic use. Differences in pain between active anodal and sham tDCS combined with transcranial ultrasound will be compared, as analyzed by a paired t-test. Regarding potential differences in baseline values, because differences between post-stimulation vs. pre-stimulation will be studied, this would address potential differences in baseline values.

Statistical analysis (Aim 2): The outcome here will be mechanical and pressure pain levels (mechanical threshold will be the primary outcome and the pressure pain will be the secondary outcome) and the independent variables will be group of stimulation (anodal vs. sham tDCS with ultrasound). This will be tested by comparing differences in changes of pain threshold between anodal and sham tDCS using ANOVA. If ANOVA shows significant differences a paired t-test (if the data are not normal, we will use a non-parametric approach) will then be performed to test whether pain thresholds between anodal and sham tDCS combined with transcranial ultrasound are significantly different. As in the other tests, mechanical pain threshold will be considered as the main outcome and other thresholds will be analyzed as the secondary outcome. This aims to answer if stimulation affects the outcome (assuming that the stimulation will improve pain more than sham).

Finally pressure pain and mechanical pain thresholds will be correlated with changes in clinical outcomes (specifically with changes in pain) using Pearson's correlation test.

Statistical analysis (Aim 3): The outcome here will be flow velocity from the MCA, ACA, and PCA relative to baseline (i.e., pre vs. post stimulation) and the independent variable will be group of stimulation (anodal vs. sham tDCS with ultrasound). This will be tested by comparing differences in changes in the flow velocities between anodal and sham tDCS combined with transcranial ultrasound using ANOVA. If ANOVA shows significant differences we will then perform a 3 paired t-tests (if the data are not normal, we will use a non-parametric approach) to test whether the change in flow velocities between anodal and sham tDCS combined with transcranial ultrasound are significantly different.

What is claimed is:

1. A method for treating osteoarthritis, the method comprising:
   providing one or more noninvasive transcranial stimulation sources; and
   providing, via the one or more noninvasive transcranial stimulation sources, a combination of transcranial electrical energy and transcranial mechanical energy that is delivered transcranially through C3/C4 in a manner that generates one or more currents within a region of a brain of the subject beneath C3/C4 that disperse from the region within the brain to thereby modulate a signal sent to or from the subject's joint, wherein the stimulation is provided over a plurality of days, thereby treating osteoarthritis.

2. The method according to claim 1, wherein the signal is a pain related signal.

3. The method according to claim 1, wherein the signal is an inflammatory related signal.

4. The method according to claim 1, wherein the signal is processed in the brain.

5. The method according to claim 1, wherein the combination of transcranial electrical energy and transcranial mechanical energy is focused to the primary motor cortex.

6. The method according to claim 1, wherein the combination of transcranial electrical energy and transcranial mechanical energy is focused to the somatosensory cortex.

7. The method according to claim 1, wherein the joint in a knee joint.

8. The method according to claim 1, wherein the method further comprises analyzing a target region of a subject to determine where to locate the one or more noninvasive transcranial stimulation sources.

* * * * *